(12) United States Patent
Bozik et al.

(10) Patent No.: US 12,370,176 B2
(45) Date of Patent: Jul. 29, 2025

(54) METHODS OF USE FOR KV7 CHANNEL ACTIVATORS

(71) Applicant: Biohaven Therapeutics Ltd., New Haven, CT (US)

(72) Inventors: Michael E. Bozik, Pittsburgh, PA (US); Steven Dworetzky, Jefferson Hills, PA (US); Kelly Picchione, Pittsburgh, PA (US); Gregory Hebrank, Greensburg, PA (US); Thomas Petzinger, Jr., Pittsburgh, PA (US)

(73) Assignee: Biohaven Therapeutics Ltd., Tortola (VG)

( * ) Notice: Subject to any disclaimer, the term of this patent is extended or adjusted under 35 U.S.C. 154(b) by 784 days.

(21) Appl. No.: 17/641,607

(22) PCT Filed: Sep. 17, 2020

(86) PCT No.: PCT/US2020/051171
§ 371 (c)(1),
(2) Date: Mar. 9, 2022

(87) PCT Pub. No.: WO2021/055538
PCT Pub. Date: Mar. 25, 2021

(65) Prior Publication Data
US 2022/0323417 A1    Oct. 13, 2022

Related U.S. Application Data

(60) Provisional application No. 62/945,300, filed on Dec. 9, 2019, provisional application No. 62/901,621, filed on Sep. 17, 2019.

(51) Int. Cl.
*A61K 31/4184* (2006.01)
*A61P 25/00* (2006.01)

(52) U.S. Cl.
CPC .......... *A61K 31/4184* (2013.01); *A61P 25/00* (2018.01)

(58) Field of Classification Search
None
See application file for complete search history.

(56) References Cited

U.S. PATENT DOCUMENTS

| 2016/0075663 A1 | 3/2016 | Resnick et al. |
| 2017/0114022 A1 | 4/2017 | Harried et al. |
| 2018/0148419 A1 | 5/2018 | Resnick et al. |
| 2019/0284142 A1 | 9/2019 | Bozik et al. |

FOREIGN PATENT DOCUMENTS

| WO | 2009074591 A1 | 6/2009 |
| WO | 2010010380 A1 | 1/2010 |
| WO | 2012004698 A1 | 1/2012 |
| WO | 2018081825 A1 | 5/2018 |
| WO | 2018158256 A2 | 9/2018 |

OTHER PUBLICATIONS

Gomis-Perez 2018 Epilepsia. 2019;60:139-148. (Year: 2018).*
International Search Report dated Feb. 22, 2021 issued for International Application No. PCT/US2020/051171 (5 pages).
Written Opinion dated Feb. 22, 2021 issued for International Application No. PCT/US2020/051171 (7 pages).
International Preliminary Report on Patentability dated Mar. 15, 2022 issued for International Application No. PCT/US2020/051171 (8 pages).
Park B.K. et al. "Metabolism of Fluorine-Containing Drugs" Annu. Rev. Pharmacol. Toxicol. 2001, 41, 443-470.
Millichap et al. "KCNQ2 encephalopathy: Features, mutational hot spots, and ezogabine treatment of 11 patients" Neurol Genet. 2016, 2:e96, doi: 10.1212/NXG.0000000000000096.

* cited by examiner

*Primary Examiner* — Danah Al-Awadi
*Assistant Examiner* — Donna M Nestor

(57) ABSTRACT

Provided herein are compounds and pharmaceutical compositions comprising a therapeutically effective amount of such compounds, or pharmaceutically acceptable salts, and a pharmaceutically acceptable excipient, and methods of treating neurodevelopmental diseases or disorders (NDD) and developmental and epileptic encephalopathy (DEE), comprising administering such compounds, or pharmaceutically acceptable salts, and pharmaceutical compositions, to pediatric patients.

11 Claims, 30 Drawing Sheets

KCNQ2 W236L ural disorder disorder disorder disorder...

METHODS OF USE FOR KV7 CHANNEL ACTIVATORS

CROSS-REFERENCE TO RELATED APPLICATIONS

This application is the United States national phase under 35 U.S.C. § 371 of International Application No. PCT/US2020/051171 filed Sep. 17, 2020, which claims the benefit of U.S. Provisional Application No. 62/901,621 filed Sep. 17, 2019 and U.S. Provisional Application No. 62/945,300 filed Dec. 9, 2019, the disclosures of which are incorporated herein by reference in their entirety.

GOVERNMENT INTERESTS

This invention was made with United States Government support under Grant No. U44NS093160 awarded by the National Institute of Neurological Disorders and Stroke of the National Institutes of Health. The United States Government has certain rights in the invention.

SUMMARY OF INVENTION

Embodiments described herein are directed to methods of treating a neurodevelopmental disease or disorder comprising administering a therapeutically effective amount of a Compound A, or pharmaceutically acceptable salt thereof, to a pediatric subject in need thereof. In some embodiments, the subject is a fetus, a neonate from birth to about 1 month, an infant from about 1 month to about 24 months, a child of about 2 years to about 11 years old, or an adolescent of about 12 years to 18 years old.

Embodiments described herein are directed to methods of treating a neurodevelopmental disease or disorder comprising administering a therapeutically effective amount of Compound A, or a pharmaceutically acceptable salt thereof, which is selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide.

Embodiments described herein are directed to methods of treating a neurodevelopmental disease or disorder (NDD) comprising administering a therapeutically effective amount of Compound A, or a pharmaceutically acceptable salt thereof, wherein the neurodevelopmental disease or disorder (NDD) is selected from the group consisting of Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, West syndrome, SCN8A-related epilepsy with encephalopathy (EIEE13), epilepsy of infancy with migrating focal seizures (EIMFS), autosomal dominant nocturnal frontal lobe epilepsy (ADNFLE), Doose syndrome, adrenoleukodystrophy (ALD), ATP6V1A encephalopathy, atypical childhood epilepsy with centrotemporal spikes (ACECTS), autosomal dominant rolandic epilepsy with speech dyspraxia (ADRESD), CDKL5 encephalopathy, childhood epilepsy with centrotemporal spikes (CECTS), epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, neuronal ceroid lipfuscinoses (NCL), non-syndromic developmental and epileptic encephalopathy, PTPN23 enchephalopathy, Rasmussen syndrome, SCN2A-related neonatal epilepsies, STXBP1 encephalopathy, tuberous sclerosis (TS)/tuberous sclerosis complex (TSC), and combinations thereof.

Embodiments described herein are directed to methods of treating a neurodevelopmental disease or disorder (NDD) comprising administering a therapeutically effective amount of Compound A, or a pharmaceutically acceptable salt thereof, wherein the neurodevelopmental disease or disorder (NDD) is selected from the group consisting of Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, West syndrome, SCN8A-related epilepsy with encephalopathy (EIEE13), epilepsy of infancy with migrating focal seizures (EIMFS), autosomal dominant nocturnal frontal lobe epilepsy (ADNFLE), and combinations thereof.

Embodiments described herein are directed to methods of treating a neurodevelopmental disease or disorder (NDD) comprising administering a therapeutically effective amount of Compound A, or a pharmaceutically acceptable salt thereof, wherein the neurodevelopmental disease or disorder (NDD) is Doose syndrome.

Embodiments described herein are directed to methods of treating a neurodevelopmental disease or disorder (NDD) comprising administering a therapeutically effective amount of Compound A, or a pharmaceutically acceptable salt thereof, wherein the neurodevelopmental disease or disorder (NDD) is selected from the group consisting of adrenoleukodystrophy (ALD), ATP6V1A encephalopathy, atypical childhood epilepsy with centrotemporal spikes (ACECTS), autosomal dominant rolandic epilepsy with speech dyspraxia (ADRESD), CDKL5 encephalopathy, childhood epilepsy with centrotemporal spikes (CECTS), epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, neuronal ceroid lipfuscinoses (NCL), non-syndromic developmental and epileptic encephalopathy, PTPN23 enchephalopathy, Rasmussen syndrome, SCN2A-related neonatal epilepsies, STXBP1 encephalopathy, tuberous sclerosis (TS)/tuberous sclerosis complex (TSC), and combinations thereof.

Embodiments described herein are directed to methods of treating a developmental and epileptic encephalopathy (DEE) comprising administering a therapeutically effective amount of Compound A, or a pharmaceutically acceptable salt thereof, wherein the developmental and epileptic encephalopathy (DEE) is selected from the group consisting of autosomal dominant nocturnal frontal lobe epilepsy (ADNFLE), Dravet syndrome, early myoclonic encephalopathy, electrical status epilepticus during sleep (ESES), epilepsy of infancy with migrating focal seizures (EIMFS), Landau Kleffner syndrome, Lennox-Gastaut syndrome, Ohtahara syndrome, SCN8A-related epilepsy with encephalopathy (EIEE13), West syndrome, Doose syndrome, ATP6V1A encephalopathy, autosomal dominant rolandic epilepsy with speech dyspraxia (ADRESD), CDKL5 encephalopathy, epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, non-syndromic developmental and epileptic encephalopathy, PTPN23 enchephalopathy, Rasmussen syndrome, SCN2A-related neonatal epilepsies, STXBP1 encephalopathy, and combinations thereof.

Embodiments described herein are directed to methods of treating a developmental and epileptic encephalopathy (DEE) comprising administering a therapeutically effective amount of Compound A, or a pharmaceutically acceptable salt thereof, wherein the developmental and epileptic encephalopathy (DEE) is selected from the group consisting of autosomal dominant nocturnal frontal lobe epilepsy (ADNFLE), Dravet syndrome, early myoclonic encephalopathy, electrical status epilepticus during sleep (ESES), epilepsy of infancy with migrating focal seizures (EIMFS), Landau Kleffner syndrome, Lennox-Gastaut syndrome, Ohtahara syndrome, SCN8A-related epilepsy with encephalopathy (EIEE13), West syndrome, and combinations thereof.

Embodiments described herein are directed to methods of treating a developmental and epileptic encephalopathy (DEE) comprising administering a therapeutically effective amount of Compound A, or a pharmaceutically acceptable salt thereof, wherein the developmental and epileptic encephalopathy (DEE) is Doose syndrome.

Embodiments described herein are directed to methods of treating a developmental and epileptic encephalopathy (DEE) comprising administering a therapeutically effective amount of Compound A, or a pharmaceutically acceptable salt thereof, wherein the developmental and epileptic encephalopathy (DEE) is selected from the group consisting of ATP6V1A encephalopathy, autosomal dominant rolandic epilepsy with speech dyspraxia (ADRESD), CDKL5 encephalopathy, Epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, non-syndromic developmental and epileptic encephalopathy, PTPN23 enchephalopathy, Rasmussen syndrome, SCN2A-related neonatal epilepsies, STXBP1 encephalopathy, and combinations thereof.

DETAILED DESCRIPTION

Figure 1:
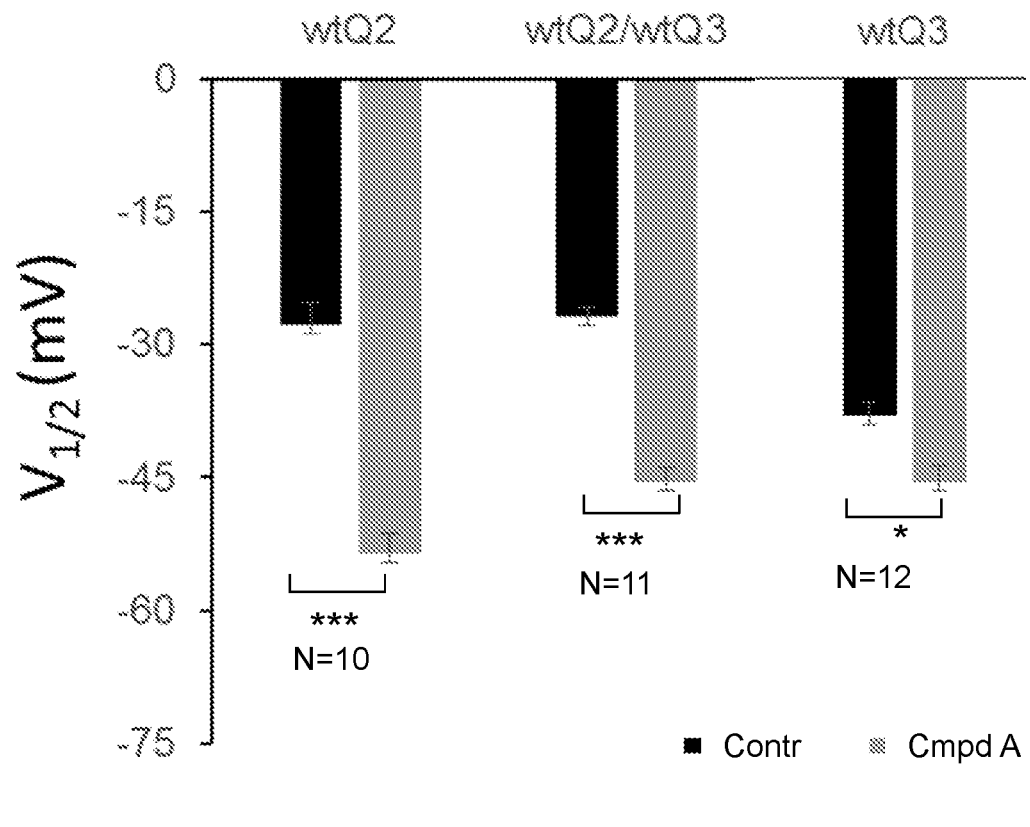
FIG. 1 demonstrates that Compound A negatively shifts activation voltage dependence more strongly for KCNQ2 homomers than for KCNQ2/Q3 heteromers and KCNQ3 homomers.

Potassium ($K^+$) channels, present on the plasma membranes of most cell types, are the most diverse class of all ion channels and are associated with a wide range of physiological functions including the regulation of the electrical properties of excitable cells. The primary pore-forming ($\alpha$) subunits of these highly selective cation channels are divided into three primary structural classes based on the number of transmembrane (TM)-spanning regions and pore (P) regions: currently there are known to be 6TM/1P, 2TM/1P and 4TM/2P $K^+$ channels. The Kv7 genes (originally termed KCNQ, a name assigned by the HUGO Gene Nomenclature Committee (HGNC)) were assigned to a subfamily of voltage-gated $K^+$ channels by the International Union of Pharmacology (IUPHAR). The Kv7 subfamily consists of five homologous pore-forming α subunits, Kv7.1-7.5, that have a structure typical of voltage-gated $K^+$ channels with 6TM-spanning regions (S1-S6) flanked by intracellular N-terminal and C-terminal domains, a typical voltage-sensor domain located in S4 comprised of alternating positively-charged residues and a single P region between S5 and S6 of each subunit. The channels are formed as tetramers of the primary α subunits, either as homotetramers or heterotetramers. Neurons are known to express Kv7 channels comprised of Kv7.2-7.5 α subunits. Some of these gene products may be exclusively neuronal while others, such as Kv7.4 and Kv7.5, can be found in other tissues such as smooth and skeletal muscle.

Native M-currents were first characterized in amphibian sympathetic neurons. M-currents were notable because they were slowly activating and non-inactivating, active at membrane potentials at or near the resting membrane potential of neurons and muscarinic cholinergic agonists produced a reduction in the M-current, demonstrating a direct and inhibitory link between G-protein coupled receptors (GPCRs) and a physiological $K^+$ current. It was not until the cloning of this subfamily of genes that the pharmacological and biophysical identity was established between Kv7.2/7.3 (and likely Kv7.3/7.5) heteromultimers and the 'M'-currents, providing significant new evidence for their importance in neuronal regulation.

The distributions of these channels, both regionally and developmentally, as well as their biophysical characteristics, support their role in providing enduring resistance to depolarizing excitatory influences. Under physiological conditions, as was demonstrated with native M-currents, they can be very effective at regulating the sub-threshold excitability of certain neuronal populations with significant roles in regulating the frequency and ultimately the pattern of action potential discharge in many types of neurons. Their importance in neuronal regulation was punctuated by the discovery that neuronal Kv7 mutations lead to benign familial neonatal convulsions (BFNC), indicating that reduction of the influence of Kv7.2 and Kv7.3 channels can dramatically alter neuronal excitability. Mutation analyses demonstrated their involvement in BFNC and suggested their utility as targets for anti-epileptic drugs (AEDs).

Mutations in Kv7.2, and less commonly in Kv7.3, were reported as the cause of autosomal dominant benign neonatal seizures (BFNS), mainly by haploinsufficiency. BFNS is an idiopathic epilepsy with seizures occurring in the first days of life and is due to mutations in both Kv7.2 and Kv7.3. Kv7.2 and Kv7.3 interact to give a current larger than the individual currents obtained as homomers. In situ hybridization shows that Kv7.2 is mainly present in the cerebellar cortex, the neocortex and the hippocampal formation, including the dentate gyrus. These three structures present distinct epileptic seizure susceptibility. Kv7.3 is localized in the same areas in mouse brain. However, Kv7.2 expression appears earlier than that of Kv7.3 and rapidly increases during the first week of life. At birth, Kv7.3 is expressed in a very low amount whereas Kv7.2 is already expressed at a significant level. Accordingly, different profiles of association of Kv7.2 and Kv7.3 occur during development.

Although BFNS usually bears an excellent long-term prognosis, seizure recurrences later in life have also been described. More recently, it was found that de novo dominant-negative mutations in the KCNQ2 gene result in a rare, devastating pediatric epileptic encephalopathy, KCNQ2 epileptic encephalopathy (KCNQ2-EE), and are responsible for 5%-23% of early infantile epileptic encephalopathies (EIEEs). Although only recently described, heterozygous de novo variants in KCNQ2 are a highly validated cause of early onset epileptic encephalopathy, and KCNQ2-EE has emerged as a well-defined clinical entity with a characteristic neonatal presentation, including hypotonia, treatment-resistant tonic seizures, a profoundly abnormal interictal EEG with prominent burst-suppression, and most often with moderate-to-profound global developmental delay, resulting from a defined subset of missense variants in the gene. Neuroimaging reveals frontal lobe hypoplasia or transient MRI signal abnormalities of the basal ganglia or thalamus in some cases. Neurodevelopment is negatively impacted in all children, even if seizure control with the use of AEDs is achieved in the initial months of life. It has been proposed that the clinical features of KCNQ2-EE could be associated with the functional consequence of mutations on M-current and could thus be predictive of the neurologic prognosis. There is a marked disparity of the impact of the known KCNQ2 mutations on Kv7.2 channel function, which vary on association with Kv7.3 subunits. Density of homomeric channels may be the most reliable property relating Kv7.2 function to encephalopathy. It is hypothesized that homomeric Kv7.2 channels play an essential role for fine-tuning neuronal connections during early brain development and correlates to the severity of the dominant-negative effects of KCNQ2 mutations causative of the encephalopathy.

The compounds provided herein are efficacious activators for the Kv7.2 homotetramer, the Kv7.3 homotetramer, the Kv7.2/7.3 heterotetramer, and based on the above expression of the Kv7.2 and Kv7.3 channels, such compounds are effective in the treatment of disorders of early infant development, neurodevelopmental disease or disorder (NDD), and developmental and epileptic encephalopathies (DEE), such as Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, West syndrome, SCN8A-related epilepsy with encephalopathy (EIEE13), epilepsy of infancy with migrating focal seizures (EIMFS), autosomal dominant nocturnal frontal lobe epilepsy (ADNFLE), Doose syndrome, adrenoleukodystrophy (ALD), ATP6V1A encephalopathy, atypical childhood epilepsy with centrotemporal spikes (ACECTS), autosomal dominant rolandic epilepsy with speech dyspraxia (ADRESD), CDKL5 encephalopathy, childhood epilepsy with centrotemporal spikes (CECTS), epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, neuronal ceroid lipfuscinoses (NCL), non-syndromic developmental and epileptic encephalopathy, PTPN23 enchephalopathy, Rasmussen syndrome, SCN2A-related neonatal epilepsies, STXBP1 encephalopathy, tuberous sclerosis (TS)/tuberous sclerosis complex (TSC), and combinations thereof.

Before the present compositions and methods are described, it is to be understood that any invention is not limited to the particular processes, compositions, or methodologies described, as these may vary. Moreover, the processes, compositions, and methodologies described in particular embodiments are interchangeable. Therefore, for example, a composition, dosage regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention, which will be limited only by the appended claims. Unless clearly defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a", "an", and "the" include plural reference unless the context clearly dictates otherwise.

As used herein, the term "about" means plus or minus 10% of the numerical value of the number with which it is being used. Therefore, about 50% means in the range of 45%-55%. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

"Administering," when used in conjunction with a therapeutic, means to administer a therapeutic directly into or onto a target tissue or to administer a therapeutic to a subject whereby the therapeutic positively impacts the tissue to which it is targeted. "Administering" a composition may be accomplished by oral administration, injection, infusion, absorption or by any method in combination with other known techniques. "Administering" may include the act of self-administration or administration by another person such as a healthcare provider or a device.

As used herein, the terms "comprising," "comprise," "comprises," and "comprised" are inclusive or open-ended and do not exclude additional, unrecited elements or method steps.

As used herein, the term "consists of" or "consisting of" means that the composition or method includes only the elements, steps, or ingredients specifically recited in the particular embodiment or claim.

As used herein, the term "consisting essentially of" or "consists essentially of" means that the composition or method includes only the specified materials or steps and those that do not materially affect the basic and novel characteristics of the claimed invention.

The term "improves" is used to convey that the present invention refers to the overall physical state of an individual to whom an active agent has been administered. For example, the overall physical state of an individual may "improve" if one or more symptoms of a condition, disease or disorder, such as epilepsy or a neurodegenerative disorder, are alleviated by administration of an active agent. "Improves" may also refer to changes in the appearance, form, characteristics, and/or physical attributes of tissue, or any combination thereof, to which it is being provided, applied, or administered.

The term "inhibit," "suppress," "decrease," "interfere," and/or "reduce" (and like terms) generally refers to the act of reducing, either directly or indirectly, a function, activity, or behavior relative to the natural, expected, or average or relative to current conditions.

The term "homomer" or "homotetramer" is used to refer to the configuration of the Kv7 channel in that all four of the subunits are of an identical type, which are either wildtype, mutant, or any combination thereof. For example, a KCNQ2 homomer or a Kv7.2 homomer is composed of four alpha subunits of Kv7.2.

The terms "heteromer" or "heterotetramer" can be used interchangeably and are used to refer to the configuration of the Kv7 channel in that the four subunits will be of two or more subtypes, which are either wildtype, mutant, or any combination thereof. For example, a KCNQ2/3 heteromer or a Kv7.2/Kv7.3 heteromer are composed of a mixed combination of Kv7.2 Kv7.3 subunits.

In each of the embodiments disclosed herein, the compositions and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

As used herein, the term "therapeutic" means an agent utilized to treat, combat, ameliorate, or prevent, or any combination thereof, an unwanted condition, disorder or disease of a subject.

As used herein, the term "patient" and "subject" are interchangeable and may be taken to mean any living organism, which may be treated with compounds of the present invention. As such, the terms "patient" and "subject" may include, but are not limited to, any non-human mammal, primate or human. In some embodiments, the "patient" or "subject" is an adult, child, infant, or fetus. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans. In certain embodiments, the human is a neonate from birth to about 1 month. In certain embodiments, the human is an infant from about 1 month to about 24 months. In certain embodiments, the human is a fetus and is treated in utero. In certain embodiments, the human is a child of about 2 years to about 11 years old. In certain embodiments, the human is an adolescent of about 12 years to 18 years old. In embodiments, the subject is a pediatric subject, which is a human fetus (treated in utero), a neonate from birth to about 1 month, an infant from about 1 month to about 24 months, a child of about 2 years to about 11 years old, or an adolescent of about 12 years to 18 years old.

The terms "therapeutically effective amount" or "therapeutic dose" as used herein are interchangeable and may refer to the amount of an active agent or pharmaceutical compound or composition that elicits a clinical, biological or medicinal response in a tissue, system, animal, individual or human that is being sought by a researcher, veterinarian, medical doctor or other clinical professional. A clinical, biological or medical response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experience or exhibited by the individual.

The term "treat," "treated," or "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disorder, disorder or condition.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol. 6, 1-19, describes pharmaceutically acceptable salts in detail. A pharmaceutically acceptable "salt" is any acid addition salt, preferably a pharmaceutically acceptable acid addition salt, including, but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethanesulfonic, ethanesulfonic, benzenesulfonic or p-toluenesufonic, acetic, malic, fumaric, succinic, citric, benzonic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

If stereochemistry is not indicated, a name or structural representation includes any stereoisomer or any mixture of stereoisomers and Applicant reserves the right to specifically identify and claim a compound as a single stereoisomer or any particular mixture of stereoisomers.

Compounds described herein may contain an asymmetric center and may thus exist as enantiomers. Where the compounds according to embodiments herein possess two or more asymmetric centers, they may additionally exist as diastereomers. Embodiments herein include all such possible stereoisomers as substantially pure resolved enantiomers, racemic mixtures thereof, as well as mixtures of diastereomers. In some embodiments, the formulas are shown without a definitive stereochemistry at certain positions. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific or stereoselective synthesis using optically pure or enantioenriched starting materials or reagents of known configuration. The scope of embodiments herein as described and claimed encompasses the racemic forms of the compounds as well as the individual enantiomers, diastereomers, and stereoisomer-enriched mixtures and Applicant reserves the right to specifically identify and claim a compound in any such form.

The compounds disclosed herein can exist as and therefore include all stereoisomers, conformational isomers and mixtures thereof in all proportions as well as isotopic forms such as deuterated compounds and Applicant reserves the right to specifically identify and claim a compound in any such form.

Compounds

Embodiments described herein are directed to the use of any one of the following compounds, or a pharmaceutically acceptable salt thereof: N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; or N-(1-(tert-butyl)-5,6-difluoro-1H-benzo[d]imidazol-2-yl)-2-(2,2,3,3-tetrafluorocyclobutyl)acetamide. The structures of these compounds can be found in Table 1. In embodiments, such compounds may be administered in a pharmaceutical composition as described herein.

TABLE 1

Compound structures

| Example Number | Structure | IUPAC |
|---|---|---|
| 352 | | N-(1-cyclobutyl-4-fluoro-6-(1-hydroxycyclobutyl)-1H-benzo[d]imidazol-2-yl)-4,4,4-trifluoro-3,3-dimethylbutanamide |

TABLE 1-continued

Compound structures

| Example Number | Structure | IUPAC |
|---|---|---|
| 393 | | N-(1-(tert-butyl)-6-(difluoromethoxy)-1H-benzo[d]imidazol-2-yl)-3,3-dimethylbutanamide |
| 401 | | N-(6-cyano-1-(1,1,1-trifluoro-2-methylpropan-2-yl)-1H-benzo[d]imidazol-2-yl)-3,3-dimethylbutanamide |
| 403 | | N-(1-cyclobutyl-4-fluoro-6-(2-hydroxypropan-2-yl)-1H-benzo[d]imidazol-2-yl)-2-(1-methylcyclopropyl)acetamide |
| 411 | | N-(6-cyano-1-cyclobutyl-4-fluoro-1H-benzo[d]imidazol-2-yl)-3,3-dimethylbutanamide |
| 417 | | N-(1-cyclobutyl-6-fluoro-1H-benzo[d]imidazol-2-yl)-3,3-dimethylbutanamide |
| 420 | | N-(1-(tert-butyl)-6-cyano-4-fluoro-1H-benzo[d]imidazol-2-yl)-3,3-dimethylbutanamide |

TABLE 1-continued

Compound structures

| Example Number | Structure | IUPAC |
|---|---|---|
| 426 | | N-(7-cyano-1-(1-methylcyclobutyl)-1H-benzo[d]imidazol-2-yl)-3-cyclopropyl-3-methylbutanamide |
| 439 | | N-(6-chloro-7-cyano-1-cyclobutyl-1H-benzo[d]imidazol-2-yl)-3,3-dimethylbutanamide |
| 449 | | N-(1-cyclobutyl-5-fluoro-1H-benzo[d]imidazol-2-yl)-3,3-dimethylbutanamide |
| 457 | | N-(1-(tert-butyl)-6-cyano-4,7-difluoro-1H-benzo[d]imidazol-2-yl)-3,3-dimethylbutanamide |
| 507 | | N-(6-cyano-1-cyclobutyl-7-(trifluoromethyl)-1H-benzo[d]imidazol-2-yl)-3,3-dimethylbutanamide |

TABLE 1-continued

Compound structures

| Example Number | Structure | IUPAC |
|---|---|---|
| 517 | | N-(6-cyano-4,7-difluoro-1-(1-methylcyclobutyl)-1H-benzo[d]imidazol-2-yl)-3,3-dimethylbutanamide |
| 530 | | N-(1-(tert-butyl)-5,7-difluoro-1H-benzo[d]imidazol-2-yl)-4,4,4-trifluoro-3,3-dimethylbutanamide |
| 557 | | N-(1-(tert-butyl)-5,6-difluoro-1H-benzo[d]imidazol-2-yl)-2-(2,2,3,3-tetrafluorocyclobutyl)acetamide |

Methods of Use

Embodiments described herein are directed to methods of treating diseases or disorders that would benefit from the activation of a Kv7.2 homomer comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide. In some embodiments, the disease or disorder is developmental and diagnosed during prenatally, neonatally, infancy, during early childhood, during adolescence, and during early adulthood. In certain embodiments, a human subject is diagnosed before birth. In certain embodiments, a neonate is diagnosed at about birth to about 1 week, or at about 1 week to about 1 month. In certain embodiments, an infant is diagnosed at about birth to about 1 week, about 1 week to about 1 month, about 1 month to about 24 months. In certain embodiments, an child is diagnosed at about birth to about 1 week, about 1 week to about 1 month, about 1 month to about 24 months, about 2 years to about 11 years. In certain embodiments, the subject is a neonate from about birth to about 1 month. In certain embodiments, the subject is an infant from about 1 month to about 24 months. In certain embodiments, the subject is a fetus and is treated in utero. In certain embodiments, the subject is a child of about 2 year to about 11 years old. In certain embodiments, the subject is an adolescent of about 12 years to 18 years old. In embodiments, the subject is a pediatric subject.

Embodiments described herein are directed to methods of treating neurodevelopmental diseases or disorders comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. In embodiments, the diseases or disorders are occurring early in life, between about 0 days to about 1 yr. The neonatal and infant brain is undergoing changes early in development and is more susceptible to alterations during this sensitive time. Studies in rodents show that KCNQ2 expression predominates over KCNQ3 early in life. The delayed expression of KCNQ3 leads to the greater density of KCNQ2 homomers relative to KCNQ2/KCNQ3 heteromers. In embodiments described herein, the method of treating developmental diseases or disorders is effective at restoring the electrical balance of the cells or normalizing the hyper-excitability caused by genes or mechanisms related to KCNQ2. In embodiments, the subject is a pediatric subject.

Embodiments described herein are directed to methods of treating neurodevelopmental diseases or disorders comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. In embodiments, the subject is a pediatric subject. In certain embodiments, the neurodevelopmental diseases or disorders are selected from the group consisting of Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, West syndrome, SCN8A-related epilepsy with encephalopathy (EIEE13), epilepsy of infancy with migrating focal seizures (EIMFS), autosomal dominant nocturnal frontal lobe epilepsy (ADNFLE), Doose syndrome, adrenoleukodystrophy (ALD), ATP6V1A encephalopathy, atypical childhood epilepsy with centrotemporal spikes (ACECTS), autosomal dominant rolandic epilepsy with speech dyspraxia (ADRESD), CDKL5 encephalopathy, childhood epilepsy with centrotemporal spikes (CECTS), epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, neuronal ceroid lipfuscinoses (NCL), non-syndromic developmental and epileptic encephalopathy, PTPN23 enchephalopathy, Rasmussen syndrome, SCN2A-related neonatal epilepsies, STXBP1 encephalopathy, tuberous sclerosis (TS)/tuberous sclerosis complex (TSC), and combinations thereof.

Embodiments described herein are directed to methods of treating neurodevelopmental diseases or disorders comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H- benzo[d]imidazol-2-yl)-2-(2,2,3,3-tetrafluorocyclobutyl)acetamide. In embodiments, the subject is a pediatric subject. In certain embodiments, the neurodevelopmental diseases or disorders are selected from the group consisting of Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, West syndrome, SCN8A-related epilepsy with encephalopathy (EIEE13), epilepsy of infancy with migrating focal seizures (EIMFS), autosomal dominant nocturnal frontal lobe epilepsy (ADNFLE), and combinations thereof.

Embodiments described herein are directed to methods of treating neurodevelopmental diseases or disorders comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide. In certain embodiments, the neurodevelopmental diseases or disorders is Doose syndrome. In embodiments, the subject is a pediatric subject.

Embodiments described herein are directed to methods of treating neurodevelopmental diseases or disorders comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide. In embodiments, the subject is a pediatric subject. In certain embodiments, the neurodevelopmental diseases or disorders are selected from the group consisting of adrenoleukodystrophy (ALD), ATP6V1A encephalopathy, atypical childhood epilepsy with centrotemporal spikes (ACECTS), autosomal dominant rolandic epilepsy with speech dyspraxia (ADRESD), CDKL5 encephalopathy, childhood epilepsy with centrotemporal spikes (CECTS), epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, neuronal ceroid lipfuscinoses (NCL), non-syndromic developmental and epileptic encephalopathy, PTPN23 enchephalopathy, Rasmussen syndrome, SCN2A-related neonatal epilepsies, STXBP1 encephalopathy, tuberous sclerosis (TS)/tuberous sclerosis complex (TSC), and combinations thereof.

Embodiments described herein are directed to methods of treating developmental and epileptic encephalopathy (DEE) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide. In embodiments, the subject is a pediatric subject. In certain embodiments, the developmental and epileptic encephalopathy (DEE) are selected from the group consisting of autosomal dominant nocturnal frontal lobe epilepsy (ADNFLE), Dravet syndrome, early myoclonic encephalopathy, electrical status epilepticus during sleep (ESES), epilepsy of infancy with migrating focal seizures (EIMFS), Landau Kleffner syndrome, Lennox-Gastaut syndrome, Ohtahara syndrome, SCN8A-related epilepsy with encephalopathy (EIEE13), West syndrome, Doose syndrome, ATP6V1A encephalopathy, autosomal dominant rolandic epilepsy with speech dyspraxia (ADRESD), CDKL5 encephalopathy, epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, non-syndromic developmental and epileptic encephalopathy, PTPN23 enchephalopathy, Rasmussen syndrome, SCN2A-related neonatal epilepsies, STXBP1 encephalopathy, and combinations thereof.

Embodiments described herein are directed to methods of treating developmental and epileptic encephalopathy (DEE) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. In embodiments, the subject is a pediatric subject. In certain embodiments, the developmental and epileptic encephalopathy (DEE) are selected from the group consisting of autosomal dominant nocturnal frontal lobe epilepsy (ADNFLE), Dravet syndrome, early myoclonic encephalopathy, electrical status epilepticus during sleep (ESES), epilepsy of infancy with migrating focal seizures (EIMFS), Landau Kleffner syndrome, Lennox-Gastaut syndrome, Ohtahara syndrome, SCN8A-related epilepsy with encephalopathy (EIEE13), West syndrome, and combinations thereof.

Embodiments described herein are directed to methods of treating developmental and epileptic encephalopathy (DEE) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. In certain embodiments, the developmental and epileptic encephalopathy (DEE) is Doose syndrome. In embodiments, the subject is a pediatric subject.

Embodiments described herein are directed to methods of treating developmental and epileptic encephalopathy (DEE) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. In embodiments, the subject is a pediatric subject. In certain embodiments, the developmental and epileptic encephalopathy (DEE) are selected from the group consisting of ATP6V1A encephalopathy, autosomal dominant rolandic epilepsy with speech dyspraxia (ADRESD), CDKL5 encephalopathy, epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (LEAD), KCNT1 epilepsy of infancy with migrating focal seizures, non-syndromic developmental and epileptic encephalopathy, PTPN23 enchephalopathy, Rasmussen syndrome, SCN2A-related neonatal epilepsies, STXBP1 encephalopathy, and combinations thereof.

Embodiments described herein are directed to methods of treating Angelman syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methyl propan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. In embodiments, the subject is a pediatric subject. Angelman syndrome is caused by loss of function of the UBE3A gene which plays a role in the normal development of the nervous system. Patients exhibit mental retardation, abnormal gait, speech impairment, seizures, and an inappropriate happy demeanor that includes frequent laughing, smiling, and excitability. They are typically treated with anticonvulsants. Compounds described herein are effective in treating the seizures associated with Angleman syndrome.

Embodiments described herein are directed to methods of treating neonatal abstinence syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methyl propan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Neonatal abstinence syndrome is seen in infants born with a dependence on drugs due to exposure in utero. At birth they may experience withdrawal symptoms including seizures. Withdrawal from opiates may cause changes in excitatory transmission. Compounds described herein reverse the excitability and ameliorate the withdrawal symptoms. In embodiments, the subject is a pediatric subject.

Embodiments described herein are directed to methods of treating early myoclonic encephalopathy, Landau Kleffner syndrome, and electrical status epilepticus during sleep comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Early myoclonic encephalopathy is diagnosed in infants that present with seizures early in life with multiple contributing factors. Seizures are treatment resistant with standard therapy and prognosis is poor. Compounds described herein are effective in treating early myoclonic encephalopathy. In embodiments, the subject is a pediatric subject.

Embodiments described herein are directed to methods of treating Ohtahara syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2- yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Ohtahara syndrome (OS) or early infantile epileptic encephalopathy (EIEE) is a rare type of epilepsy that typically becomes apparent during the first 1-3 months of life. OS may be caused by brain malformations, metabolic disorders and gene mutations, including KCNQ2. Infants have primarily tonic seizures, but may also experience partial seizures, and rarely, myoclonic seizures. Most infants with the disorder show significant underdevelopment of part or all of the cerebral hemispheres. The EEGs of infants with Ohtahara syndrome reveal a characteristic pattern of high voltage spike wave discharge followed by little activity. This pattern is known as "burst suppression." The course of Ohtahara syndrome is severely progressive. Seizures become more frequent, accompanied by delays in physical and cognitive development. Some children will die in infancy; others will survive but be profoundly handicapped. As they grow, some children will progress into other epileptic disorders, such as West syndrome or Lennox-Gestaut syndrome. Due to the early onset of disease, Kv7 channel activators are effective treatment options for this disease. In embodiments, the subject is a pediatric subject.

Embodiments described herein are directed to methods of treating autism spectrum disorders comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methyl propan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Several voltage gated potassium channels have been implicated in autistic patients including mutations and truncation in KCNQ3 gene. Dysregulation of Kv7 function facilitates seizures and impairs normal development which may result in an autistic phenotype. Autism spectrum disorder (ASD) is a developmental disorder that affects communication and behavior. Although autism can be diagnosed at any age, it is said to be a "developmental disorder" because symptoms generally appear in the first two years of life. According to the Diagnostic and Statistical Manual of Mental Disorders (DSM-5), a guide created by the American Psychiatric Association used to diagnose mental disorders, people with ASD have: 1) difficulty with communication and interaction with other people, 2) restricted interests and repetitive behaviors, and 3) symptoms that hurt the person's ability to function properly in school, work, and other areas of life. Autism is known as a "spectrum" disorder because there is wide variation in the type and severity of symptoms people experience. Compounds described herein restore synaptic transmission required for normal development. In embodiments, the subject is a pediatric subject.

Embodiments described herein are directed to methods of treating Dravet syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Mutations in the SCN1A gene which encodes a voltage-gated sodium channel are common in Dravet syndrome. Mutations cause reductions in sodium current leading to hyper-excitability of GABAergic inhibitory neurons, leading to epilepsy. More recently KCNQ2 mutations have been found to contribute to the clinical presentation of Dravet syndrome. Dravet syndrome, previously known as severe myoclonic epilepsy of infancy (SMEI), is a rare, treatment-resistant developmental epileptic encephalopathy with onset in infancy and significant neurodevelopmental, motor, cognitive, and behavioral consequences that persist into adulthood. Dravet syndrome has been characterized by prolonged febrile and non-febrile seizures within the first year of a child's life. The disease progresses to other seizure types, such as myoclonic and partial seizures, psychomotor delay, and ataxia. It is characterized by cognitive impairment, behavioral disorders, and motor deficits. Behavioral deficits often include hyperactivity and impulsiveness, and in more rare cases, autistic-like behaviors. The seizures experienced by people with Dravet syndrome become worse as the patient ages. Compounds described herein are effective in Dravet syndrome by restoring the balance of excitation and inhibition in these neurons. In embodiments, the subject is a pediatric subject.

Embodiments described herein are directed to methods of treating Lennox-Gastaut syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide. Lennox-Gastaut syndrome (LGS) is a severe, complex, and rare childhood-onset epilepsy with multifactorial cause. Evidence suggests that cortical excitability during development contributes to the disease. Changes in excitability may be secondary to brain damage. The symptoms of Lennox-Gastaut syndrome usually begin during infancy or childhood, most often between 3 to 5 years of age. Affected children experience several different types of seizures, most commonly atonic, tonic and atypical absence seizures. Tonic seizures cause an increase muscle tone and muscle stiffness. They are characterized by sustained muscle contractions that can cause mild abnormalities, such as a slight bend of the body and brief interruption of breathing, or more significant problems, such as muscle spasms of the face and flexion or extension of the arms and legs. Tonic seizures are usually brief (lasting between a few seconds and a minute) and are especially prevalent at night during sleep, but can also occur during the day. Atonic seizures cause a sudden loss of muscle tone and limpness. They can cause the head to drop or nod, problems with posture, or sudden falls. Atonic seizures are also known as drop attacks. Atonic seizures may only partially affect consciousness and usually last only a few seconds. Atypical absence seizures are associated with a period of unconsciousness usually marked by unresponsive staring. Absence seizures usually begin and end abruptly and the affected individual usually resumes activity with no memory of the episode. Absence seizures do not cause convulsions and may be so mild that they go unnoticed. They usually last only a few seconds. Children with Lennox-Gastaut syndrome may also develop cognitive dysfunction, delays in reaching developmental milestones, and behavioral problems ranging from hyperactivity and irritability to autistic symptoms and psychosis. The prognosis for LGS is poor, with a 5% mortality in childhood and persistent seizures into adulthood (80%-90%). Generally, three findings are necessary for the diagnosis: multiple generalized seizure types; a slow spike-and-wave pattern (less than 2.5 Hz) on EEG; and cognitive dysfunction. Compounds described herein normalize brain excitability, reduce seizures, and may improve development outcomes and reduce behavioral problems. In embodiments, the subject is a pediatric subject.

Embodiments described herein are directed to methods of treating Rett syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide. Rett syndrome is a rare genetic neurological disorder that occurs primarily in girls. Patients appear normal early in life, but then growth and development slow later along with the emergence of problems with walking, seizures and intellectual disability. Many cases involve mutations in the MECP2 gene which is believed to control the function of many other genes and disrupts the normal functioning of nerve cells. Upon clinical diagnosis, patients were found to have mutations in other genes including KCNQ2. Compounds described herein are an effective treatment for Rett syndrome. In embodiments, the subject is a pediatric subject.

Embodiments described herein are directed to methods of treating West syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. West syndrome is characterized by epileptic spasms and intellectual disability occurring early in life. In many cases infantile spams also includes hypsarrhythmia, a chaotic and disorganized brain activity. The diagnosis is clinical and is a combination of myoclonic jerks, developmental regression and a characteristic EEG pattern. There are many underlying causes including structural, metabolic and genetic causes all which produce a seizure disorder. Due to the early onset of disease, compounds described herein are an effective treatment option for this disease. In embodiments, the subject is a pediatric subject.

Embodiments described herein are directed to methods of treating SCN8A-related epilepsy with encephalopathy (EIEE13) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. EIEE13 is characterized by recurrent seizures, abnormal brain function, and intellectual disability; symptoms begin in infancy. Seizure frequency can be as high as hundreds per day and do not respond to current anti-epileptic medications. EIEE13 is caused by mutations in the SCN8A gene, resulting in increased Nav1.6 function. Increased Nav1.6 activity leads to excitation of neurons in the brain. Compounds described herein reduce excitability in the brain and restore normal brain function during the critical neurodevelopmental period. In embodiments, the subject is a pediatric subject.

Embodiments described herein are directed to methods of treating epilepsy of infancy with migrating focal seizures (EIMFS) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Epilepsy of infancy with migrating focal seizures (EIMFS) is also referred to as migrating partial epilepsy in infancy, migrating partial seizures of infancy, and malignant migrating partial seizures in infancy. EIMFS is a rare epilepsy syndrome where seizures begin within the first weeks of life. Seizures are focal but will migrate to different parts of the brain. Autonomic changes (stop breathing, turning blue, sweating, and hiccups) can frequently be seen during the seizures. EIMFS is associated with mutations in several genes including the KCNT1 potassium channel which accounts for 40% of EIMFS cases. KCNT1 channels contribute to the resting membrane potential and neuronal firing. Compounds described herein are effective in treating EIMFS. In embodiments, the subject is a pediatric subject.

Embodiments described herein are directed to methods of treating autosomal dominant nocturnal frontal lobe epilepsy (ADNFLE) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. ADNFLE is an uncommon form of epilepsy beginning early in childhood. Seizures typically occur at night while the person is sleeping. Seizures tend to cluster and may present with sudden repetitive movements and vocalization. ADNFLE is caused by mutations in genes encoding nicotinic acetylcholine receptors which play and important role in signaling between nerve cells and the brain. Disruption in neuronal network is associated with seizures. Kv7 activation could restore normal brain function and prevent seizures during this critical developmental period. Compounds described herein are effective in treating ADNFLE. In embodiments, the subject is a pediatric subject.

Embodiments described herein are directed to methods of treating Doose syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Doose syndrome, also known as myoclonic astatic epilepsy (MAE), is an epilepsy syndrome of early childhood that more commonly affects boys than girls with onset commonly occurring between ages 2 to 6. Children with Doose syndrome develop multiple seizure types, including drop attacks. About a third of children may have episodes of non-convulsive status epilepticus. Childhood development prior to the onset of seizures is usually normal. With frequent seizures, development slows and may regress. Compounds described herein are effective in treating Doose syndrome. In embodiments, the subject is a pediatric subject.

Embodiments described herein are directed to methods of treating adrenoleukodystrophy (ALD) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating adrenoleukodystrophy (ALD). In embodiments, the subject is a pediatric subject.

Embodiments described herein are directed to methods of treating ATP6V1A encephalopathy comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating ATP6V1A encephalopathy. In embodiments, the subject is a pediatric subject.

Embodiments described herein are directed to methods of treating atypical childhood epilepsy with centrotemporal spikes (ACECTS) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating atypical childhood epilepsy with centrotemporal spikes (ACECTS). In embodiments, the subject is a pediatric subject.

Embodiments described herein are directed to methods of treating autosomal dominant rolandic epilepsy with speech dyspraxia (ADRESD) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating autosomal dominant rolandic epilepsy with speech dyspraxia (ADRESD). In embodiments, the subject is a pediatric subject.

Embodiments described herein are directed to methods of treating CDKL5 encephalopathy comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methyl propan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1- methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating CDKL5 encephalopathy. In embodiments, the subject is a pediatric subject.

Embodiments described herein are directed to methods of treating childhood epilepsy with centrotemporal spikes (CECTS) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating childhood epilepsy with centrotemporal spikes (CECTS). In embodiments, the subject is a pediatric subject.

Embodiments described herein are directed to methods of treating epileptic encephalopathy with continuous spike-and-wave during sleep syndrome (ECSWS) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating epileptic encephalopathy with continuous spike-and-wave during sleep syndrome (ECSWS). In embodiments, the subject is a pediatric subject.

Embodiments described herein are directed to methods of treating GRIN1 encephalopathy comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating GRIN1 encephalopathy. In embodiments, the subject is a pediatric subject.

Embodiments described herein are directed to methods of treating GRIN2A epilepsy-aphasia syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3- methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating GRIN2A epilepsy-aphasia syndrome. In embodiments, the subject is a pediatric subject.

Embodiments described herein are directed to methods of treating GRIN2B encephalopathy comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating GRIN2B encephalopathy. In embodiments, the subject is a pediatric subject.

Embodiments described herein are directed to methods of treating intermediate epilepsy-aphasia disorder (IEAD) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating KCNT1 epilepsy of infancy with migrating focal seizures. In embodiments, the subject is a pediatric subject.

Embodiments described herein are directed to methods of treating neuronal ceroid lipfuscinoses (NCL) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1- methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating neuronal ceroid lipfucinoses (NCL). In embodiments, the subject is a pediatric subject.

Embodiments described herein are directed to methods of treating non-syndromic developmental and epileptic encephalopathy comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating non-syndromic developmental and epileptic encephalopathy. In embodiments, the subject is a pediatric subject.

Embodiments described herein are directed to methods of treating PTPN23 enchephalopathy comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methyl propan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating PTPN23 enchephalopathy. In embodiments, the subject is a pediatric subject.

Embodiments described herein are directed to methods of treating Rasmussen syndrome comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating Rasmussen syndrome. In embodiments, the subject is a pediatric subject.

Embodiments described herein are directed to methods of treating SCN2A-related neonatal epilepsies comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating SCN2A-related neonatal epilepsies. In embodiments, the subject is a pediatric subject.

Embodiments described herein are directed to methods of treating STXBP1 encephalopathy comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating STXBP1 encephalopathy. In embodiments, the subject is a pediatric subject.

Embodiments described herein are directed to methods of treating tuberous sclerosis (TS)/tuberous sclerosis complex (TSC) comprising administering to a subject in need thereof a therapeutically effective amount of a compound, or a pharmaceutically acceptable salt thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methyl cyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl)acetamide. Compounds described herein are effective in treating tuberous sclerosis (TS)/tuberous sclerosis complex (TSC). In embodiments, the subject is a pediatric subject.

In some embodiments, administering a therapeutically effective amount of a compound, or a pharmaceutically acceptable salt thereof, of Table 1 may include administering daily doses of about 0.1 mg to about 1,500 mg, about 1 mg to about 1,500 mg, about 10 mg to about 1,500 mg, about 50 mg to about 1,500 mg, about 75 mg to about 1,500 mg, about 100 mg to about 1,500 mg, about 125 mg to about 1,500 mg, about 150 mg to about 1,500 mg, about 175 mg to about 1,500 mg, about 200 mg to about 1,500 mg, about 225 mg to about 1,500 mg, about 250 mg to about 1,500 mg, about 275 mg to about 1,500 mg, about 300 mg to about 1,500 mg, about 350 mg to about 1,500 mg, about 400 mg to about 1,500 mg, about 450 mg to about 1,500 mg, about 500 mg to about 1,500 mg, about 550 mg to about 1,500 mg, about 600 mg to about 1,500 mg, about 650 mg to about 1,500 mg, about 700 mg to about 1,500 mg, about 750 mg to about 1,500 mg, about 800 mg to about 1,500 mg, about 850 mg to about 1,500 mg, about 900 mg to about 1,500 mg, about 950 mg to about 1,500 mg, about 1,000 mg to about 1,500 mg, and about 1,200 mg to about 1,500 mg.

In some embodiments, the therapeutically effective amount of a compound, or a pharmaceutically acceptable salt thereof, of Table 1 is selected from the group consisting of from about 0.1 mg to about 1,000 mg, about 50 mg to about 1,000 mg per day, about 100 mg to about 1,000 mg per day, about 150 mg to about 1,000 mg per day, about 300 mg to about 1,000 mg per day, about 50 mg to about 300 mg per day, and about 150 mg to about 300 mg per day.

Such therapeutically effective amounts may be administered once a day or in equal, divided doses twice a day, three times a day, or four times a day. In some embodiments, administering a therapeutically effective amount comprises administering a dose equal to about half of a daily dose twice per day. In some embodiments, the dose is administered every about 12 hours. In some embodiments, administering a therapeutically effective amount comprises administering about 1 mg two times per day, about 5 mg two times per day, about 10 mg two times per day, about 25 mg two times per day, about 75 mg two times per day, about 150 mg two times per day, about 300 mg two times per day, or about 500 mg two times per day.

Pharmaceutical Compositions

Embodiments herein are directed to pharmaceutical compositions comprising a therapeutically effective amount of a compound, or pharmaceutically acceptable salts thereof, selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(6-cyano-1-(1,1,1-trifluoro-2-methylpropan-2-yl)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl)acetamide; N-(6-cyano-1-cyclobutyl-4-fluoro-1H-benzo[d]imidazol-2-yl)-3,3-dimethylbutanamide; N-(1-cyclobutyl-6-fluoro-1H-benzo[d]imidazol-2-yl)-3,3-dimethylbutanamide; N-(1-(tert-butyl)-6-cyano-4-fluoro-1H-benzo[d]imidazol-2-yl)-3,3-dimethylbutanamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-cyclobutyl-5-fluoro-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-1-cyclobutyl-7-(trifluoromethyl)-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide. Pharmaceutical formulations containing such compounds and a suitable carrier can be in various forms including, but not limited to, solids, solutions, powders, fluid emulsions, fluid suspensions, semi-solids, and dry powders including an effective amount of a compound of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's, The Pharmaceutical Basis of Therapeutics, 6th Edition, MacMillan Publishing Co., New York (1980) both of which are hereby incorporated by reference in their entireties can be consulted.

In some embodiments, a single unit dose of a compound, or a pharmaceutically acceptable salt thereof, of Table 1 is selected from the group consisting of about 0.1 mg to about 1,500 mg, about 1 mg to about 1,500 mg, about 10 mg to about 1,500 mg, about 50 mg to about 1,500 mg, about 75 mg to about 1,500 mg, about 100 mg to about 1,500 mg, about 125 mg to about 1,500 mg, about 150 mg to about 1,500 mg, about 175 mg to about 1,500 mg, about 200 mg to about 1,500 mg, about 225 mg to about 1,500 mg, about 250 mg to about 1,500 mg, about 275 mg to about 1,500 mg, about 300 mg to about 1,500 mg, about 400 mg to about 1,500 mg, about 450 mg to about 1,500 mg, about 500 mg to about 1,500 mg, about 600 mg to about 1,500 mg, about 700 mg to about 1,500 mg, about 800 mg to about 1,500 mg, about 1,000 mg to about 1,500 mg, and about 1,200 mg to about 1,500 mg.

In some embodiments, a single unit dose amount of a compound, or a pharmaceutically acceptable salt thereof, of Table 1 is selected from group consisting of about 25 mg to about 5,000 mg, about 50 mg to about 5,000 mg, about 100 mg to about 5,000 mg, about 150 mg to about 5,000 mg, about 200 mg to about 5,000 mg, about 250 mg to about 5,000 mg, about 300 mg to about 5,000 mg, about 400 mg to about 5,000 mg, about 450 mg to about 5,000 mg, about 5,000 mg, about 100 mg to about 3,000 mg, about 150 mg to about 3,000 mg, about 200 mg to about 3,000 mg, about 250 mg to about 3,000 mg, about 300 mg to about 3,000 mg, about 400 mg to about 3,000 mg, 450 mg to about 3,000 mg, about 100 mg to about 1,000 mg, about 150 mg to about 1,000 mg, about 200 mg to about 1,000 mg, about 250 mg to about 1,000 mg, about 300 mg to about 1,000 mg, about 400 mg to about 1,000 mg, about 450 mg to about 1,000 mg, about 500 mg to about 1000 mg, and about 600 mg to about 1,000 mg. In some embodiments, the single unit dose amount may be 10 mg/day to 1,500 mg/day, or about 100 mg/day to 600 mg/day. In some embodiments, such single unit doses may be administered once per day or multiple times per day, such as twice per day or three times per day.

In some embodiments, the single unit dose further comprises a pharmaceutically acceptable carrier.

The compounds can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents.

Injectable preparations may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution.

Other embodiments include a compound prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of a compound of the invention in solid dosage form may vary. For example, in one embodiment, a liquid or gelatin formulation may be prepared by combining a compound, such as those described above, and adding a thickening agent to the liquid mixture to form a gelatin. The gelatin may then be encapsulated in unit dosage form to form a capsule. In another exemplary embodiment, an oily preparation of a compound prepared as described above may be lyophilized to for a solid that may be mixed with one or more pharmaceutically acceptable excipient, carrier or diluent to form a tablet.

Further embodiments which may be useful for oral administration of a compound for the invention include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, the compounds described herein can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

EXAMPLES

Example 1: Activation of KCNQ2

The M-current is described as a non-inactivating potassium current resulting from activation on Kv7 channels. The M-current results from the combination of two distinct Kv7 subunits forming a heteromer. Kv7.3 can combine with either Kv7.2 or Kv7.5. In addition, the Kv7 subunits can form functional homomers. The assembly of subunits into homomer or heteromers is believed to be based on developmental and special regulation of expression. Importantly, the heteromers have larger currents as well as distinct permeation and conductive properties compared to the homomers. The data herein describes the preferential activation of Kv7.2 over Kv7.2/7.3 or Kv7.3 by Compound A.

Biological Assay Methods—Using lipid mediated transfection, plasmids including only wildtype (wt) KCNQ2, only wt KCNQ3, or both wt KCNQ2 and wt KCNQ3 subunits were expressed in Chinese hamster ovary (CHO) cells. Whole cell voltage-clamp protocols were used to measure gating and conductance density of wt channels before, during and after test compound application via focal pipette perfusion. The half-activating voltage ($V_{1/2}$) was determined by Boltzmann fits of the conductance-voltage (G/V) curves.

FIG. 1 demonstrates that Compound A (a compound set forth in Table 1) shifts the activation voltage dependence in cells. Compound A negatively shifts, in a significant amount, the activation voltage dependence for KCNQ2 and KCNQ3 homomers as well as KCNQ2/Q3 heteromers. The magnitude of shift is dependent on KCNQ subunit composition with KCNQ2>KCNQ2/Q3>KCNQ3.

Figure 2:
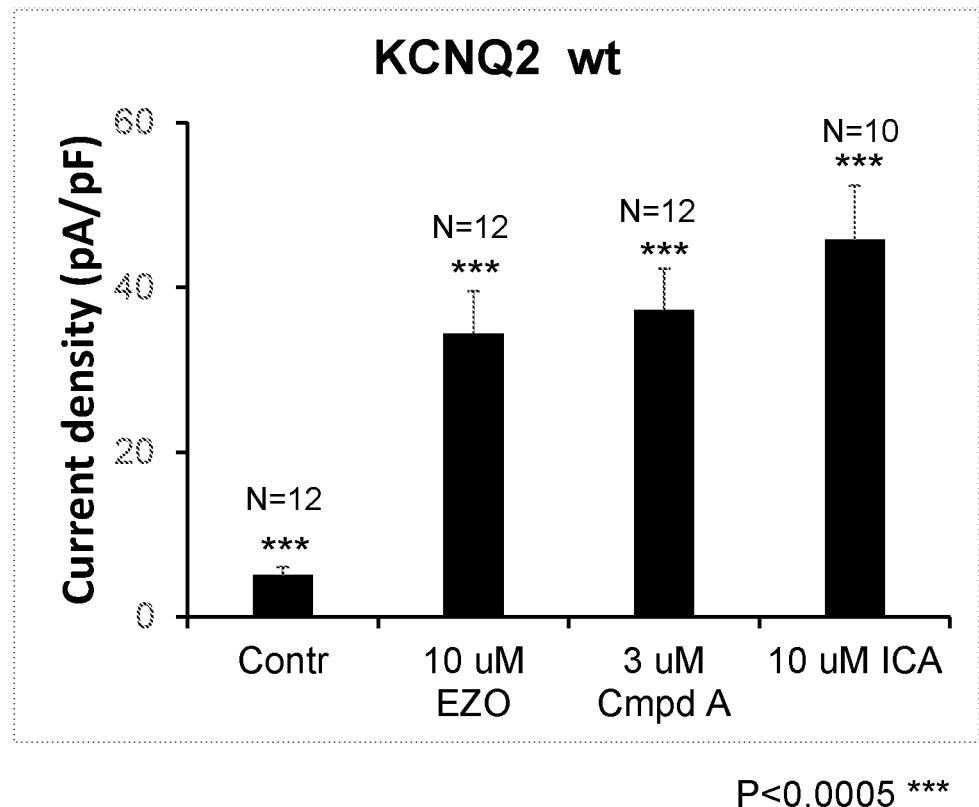
FIG. 2 demonstrates Compound A activation of KCNQ2 homomers.

FIG. 2 demonstrates that Compound A has the ability to activate Kv7.2 homomers. The current density from 3 µM Compound A is significantly increased from control. The current density activation from Compound A at 3 µM is similar to that produced by 10 µM ezogabine or ICA-069673.

Example 2: Comparison of Compound A to Ezogabine in Homomeric and Heteromeric KCNQ2 Channels Heterozygous KCNQ2 de novo variants (DNVs) are a cause of KCNQ2 epileptic encephalopathy (KCNQ2-EE). Most KCNQ2-EE variants are missense, and are clustered in hotspots that are domains for key protein functions, namely voltage sensing, trans-membrane ion flow, and sites regulating PIP2 and calmodulin binding. Under voltage-clamp, many KCNQ2-EE DNVs exert dominant-negative effects when co-expressed with wild type (wt) subunits to mimic heterozygosity. Ezogabine (EZO) increases currents through channels containing mutated subunits in vitro and has been used in KCNQ2-EE patients. Novel small molecules acting as potent neuronal KCNQ channel openers are candidate precision medicines for KCNQ2-EE.

Figure 3:
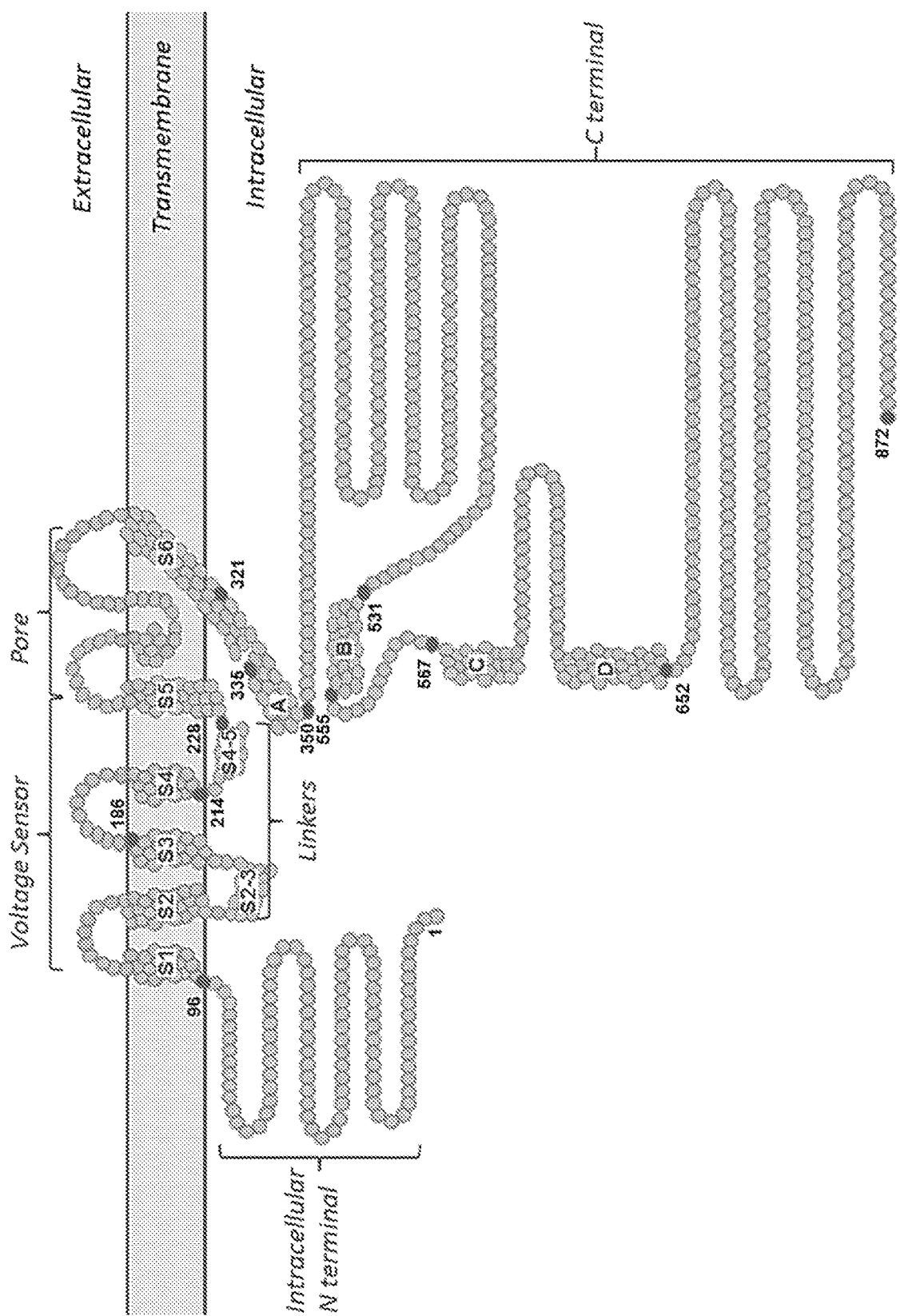
FIG. 3 depicts the KCNQ2 subunit membrane folding pattern showing locations of some recurrent pathogenic KCNQ2 EE variants.

Four highly recurrent KCNQ2-EE missense variants (FIG. 3), R210H (located in S4 of the voltage-sensor), T274M (located in the pore helix), A294V (located at the border of the pore loop and S6), and R581Q/L (located in the intracellular helix C), were introduced into KCNQ2 cDNA by QuikChange site-directed mutagenesis. R210H is in S4 of the voltage-sensor, T274M is in the pore helix, A294V is at the border of the pore loop and S6, and R581Q is in the intracellular helix C. Using lipid-mediated transfection, plasmids including the pathogenic variants were co-expressed with wildtype KCNQ2 or KCNQ2 and KCNQ3 subunits in Chinese hamster ovary (CHO) cells. The KCNQ2 S5 helix mutation W236L, which abolishes EZO modulation, was used to characterize Compound A binding. Whole cell voltage-clamp protocols were used to measure gating and conductance of wildtype channels and mutated subunit containing channels, before, during and after Compound A application via focal pipette perfusion.

Figure 4:
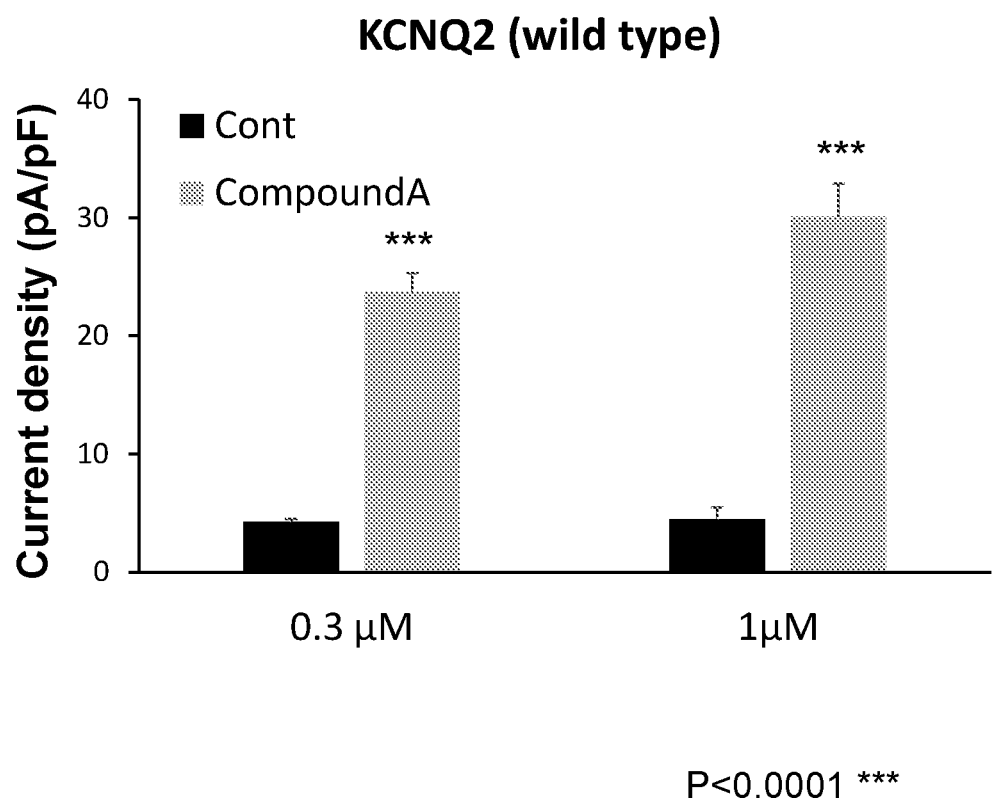
FIG. 4 demonstrates that Compound A (0.3 µM and 1.0 µM) increases homomeric channel density at −40 mV in wild type KCNQ2.
Figure 5:
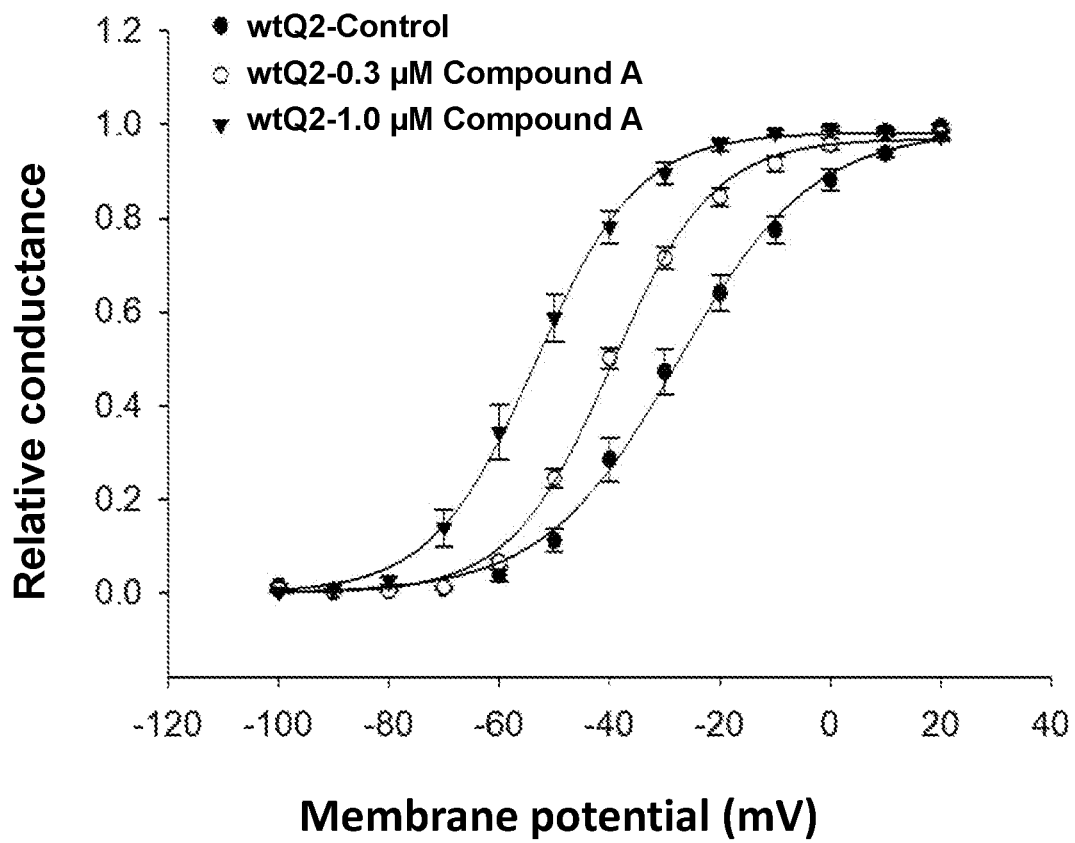
FIG. 5 demonstrates that Compound A left-shifts the homomeric KCNQ2 G/V curve with filled circles representing wild type KCNQ2, open circles representing wild type KCNQ2 in the presence of 0.3 µM of Compound A, and filled triangles representing wild type KCNQ2 in the presence of 1.0 µM of Compound A.
Figure 6:
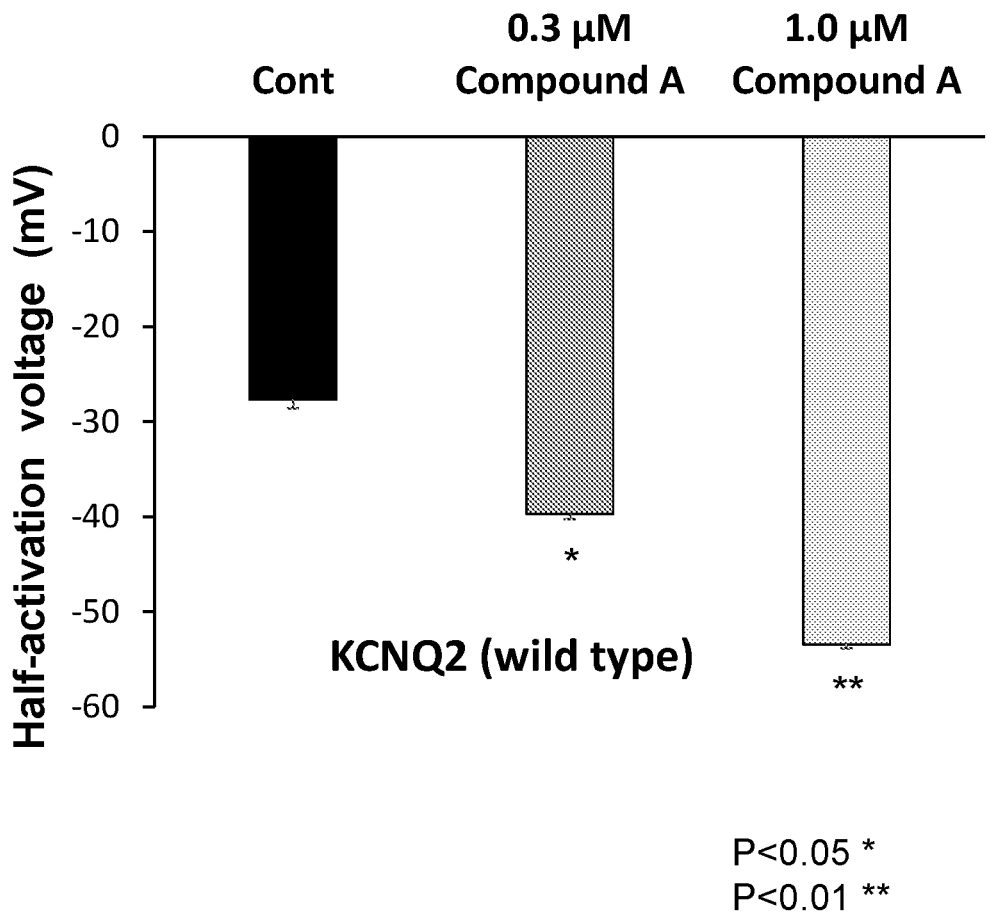
FIG. 6 depicts the half activation voltage (mV) of homomeric wild type KCNQ2 and homomeric wild type KCNQ2 with Compound A (0.3 µM and 1.0 µM).
Figure 7:
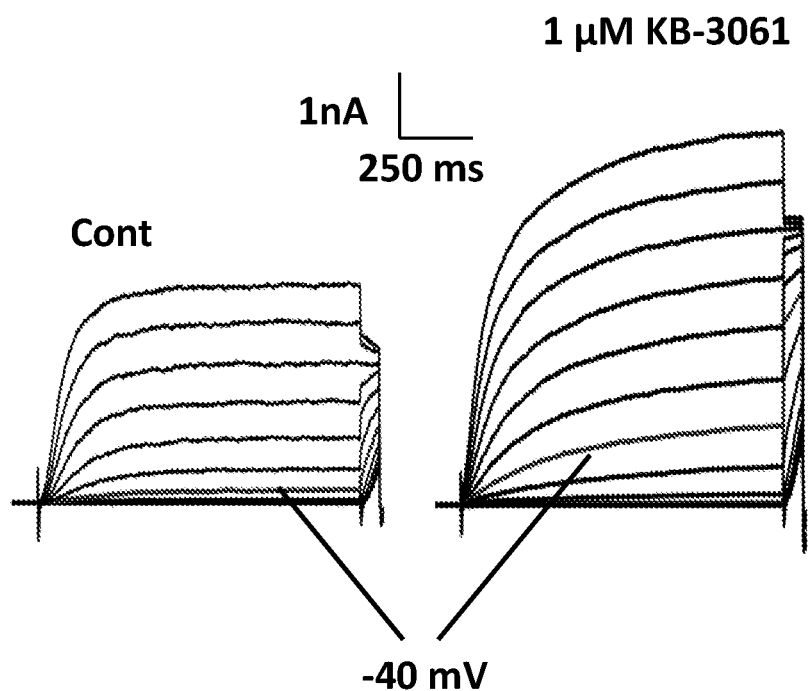
FIG. 7 depicts currents recorded from a cell expressing heteromeric wild type KCNQ2/wild type KCNQ3 channels, before and during application of 1.0 µM Compound A.
Figure 8:
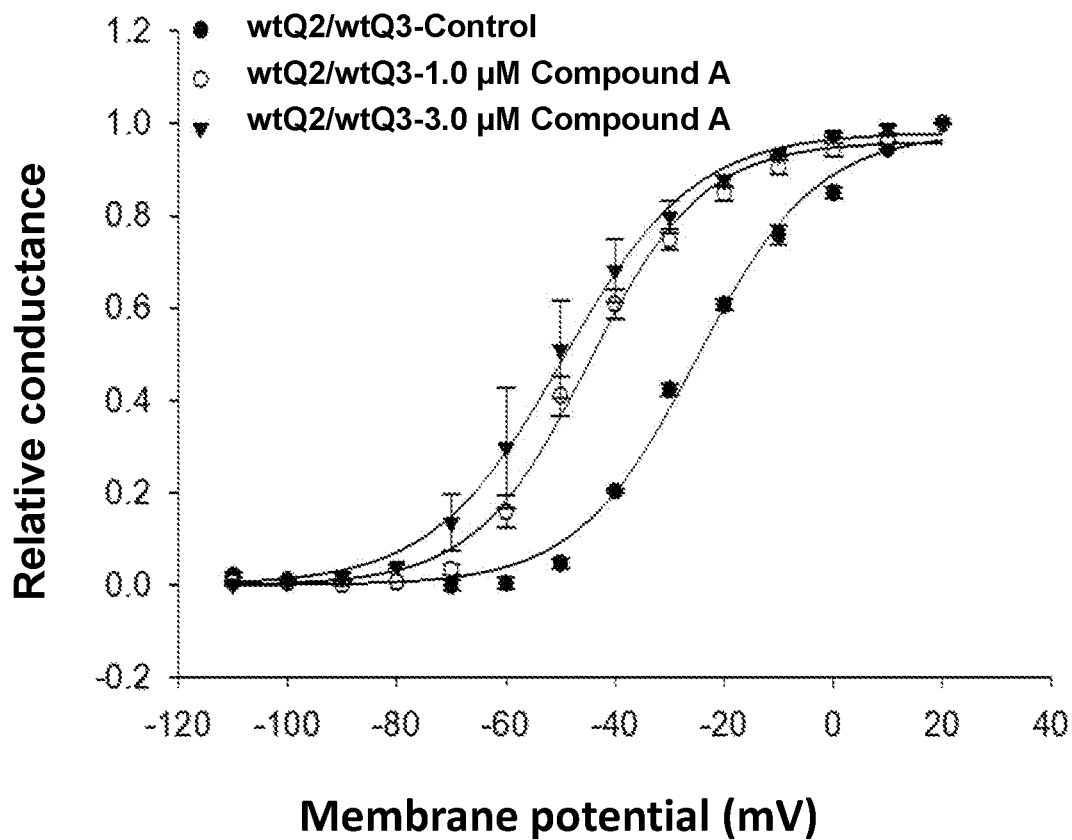
FIG. 8 demonstrates that Compound A left-shifts the heteromeric KCNQ2/wild type KCNQ3 G/V curve with filled circles representing wild type KCNQ2/wild type KCNQ3, open circles representing wild type KCNQ2/wild type KCNQ3 in the presence of 1.0 µM of Compound A, and filled triangles representing wild type KCNQ2/wild type KCNQ3 in the presence of 3.0 µM of Compound A.
Figure 9:
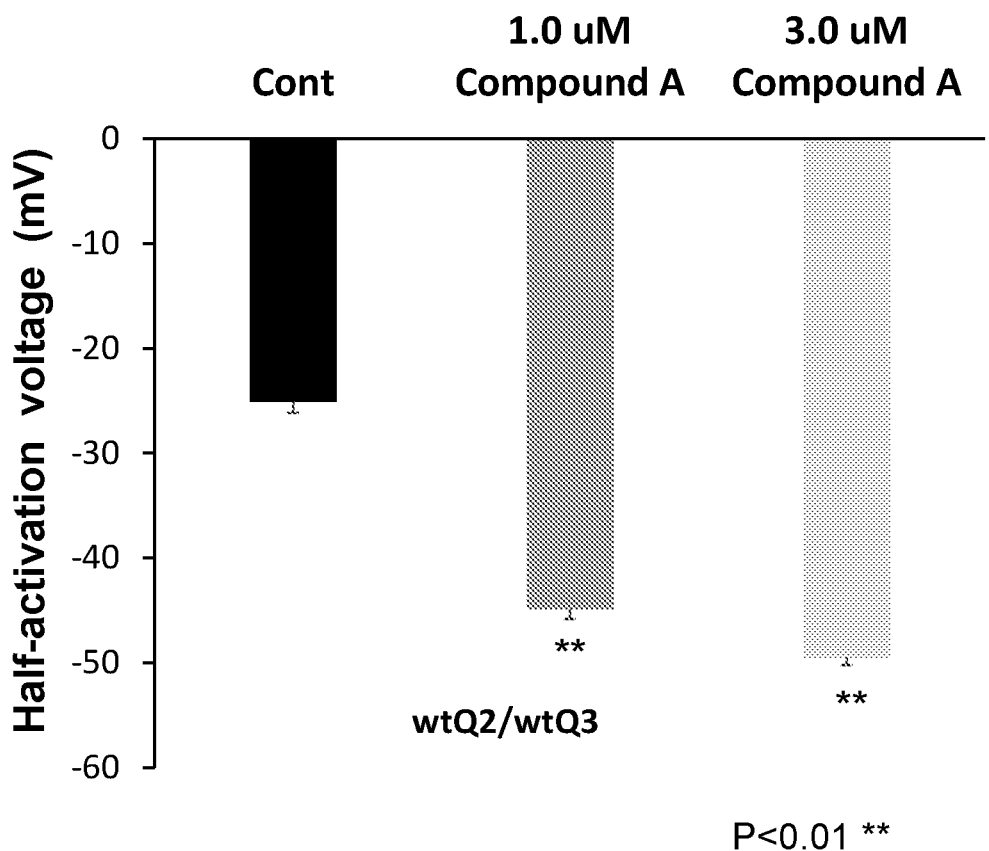
FIG. 9 depicts the half activation voltage (mV) of heteromeric wild type KCNQ2/KCNQ3 and heteromeric wild type KCNQ2/wild type KCNQ3 channels with Compound A (1.0 µM and 3.0 µM).

Compound A increases currents and shifts the G/V curve of wildtype homomeric (FIGS. 4-6) and heteromeric (FIGS. 7-9) channels. (FIG. 4) Compound A (0.3 µM and 1.0 µM) increases homomeric channel density at −40 mV (FIG. 5) and (FIG. 6) Compound A left-shifts the homomeric KCNQ2 G/V curve. (FIG. 7) representative currents recorded from a cell expressing heteromeric wild type KCNQ2/KCNQ3 channels, before and during application of 1.0 µM Compound A. (FIG. 8) and (FIG. 9) Compound A left-shifted these heteromeric wildtype channels (N=3-10 cells; *<0.05, <0.01 and *<0.001).

Figure 10:
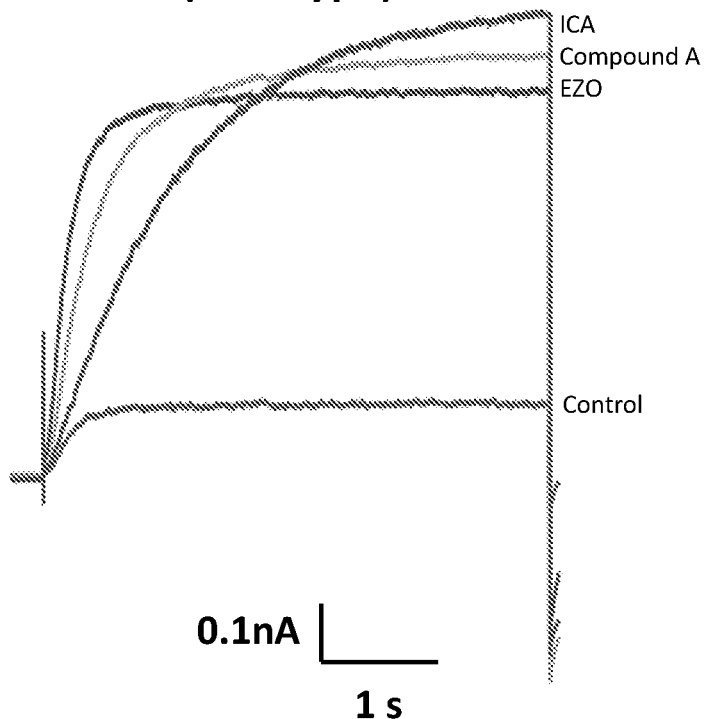
FIG. 10 depicts traces recorded at −40 mV from cells expressing wild type KCNQ2 when treated with 3.0 µM of Compound A, 10.0 µM of ezogabine, and 10.0 µM of ICA-069679 (ICA).
Figure 11:
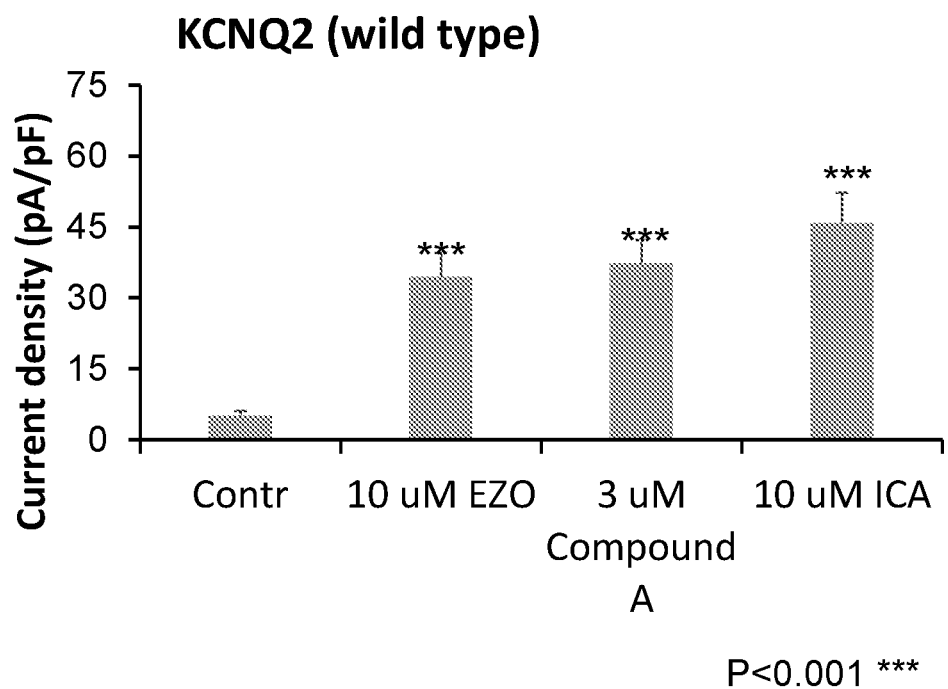
FIG. 11 depicts the current density of wild type KCNQ2 channels after treatment with 10.0 µM of ezogabine, 3.0 µM of Compound A, and 10.0 µM of ICA.
Figure 12:
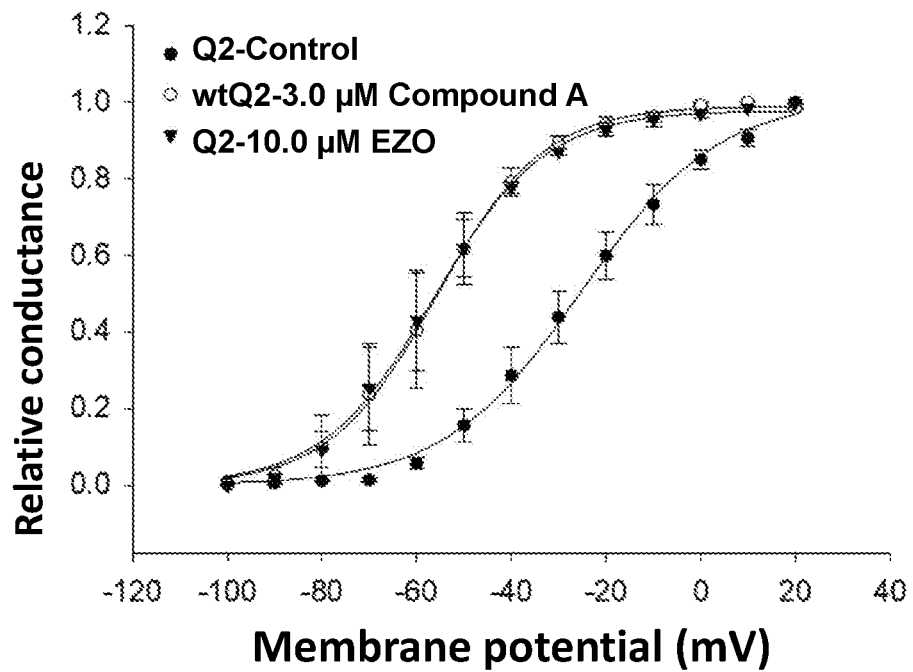
FIG. 12 depicts the effects of Compound A and EZO on the KCNQ2 G/V curve with filled circles representing wild type KCNQ2, open circles representing wild type KCNQ2 in the presence of 3.0 µM of Compound A, and filled triangles representing wild type KCNQ2 in the presence of 10.0 µM of EZO.
Figure 13:
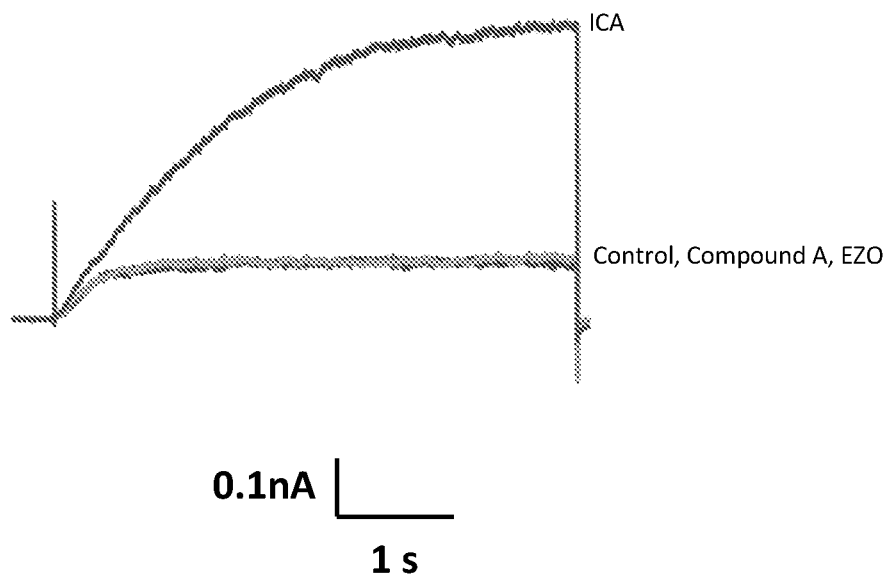
FIG. 13 depicts traces recorded at −40 mV from cells expressing KCNQ2 W236L when treated with 3.0 µM of Compound A, 10.0 µM of ezogabine, and 10.0 µM of ICA-069679 (ICA).
Figure 14:
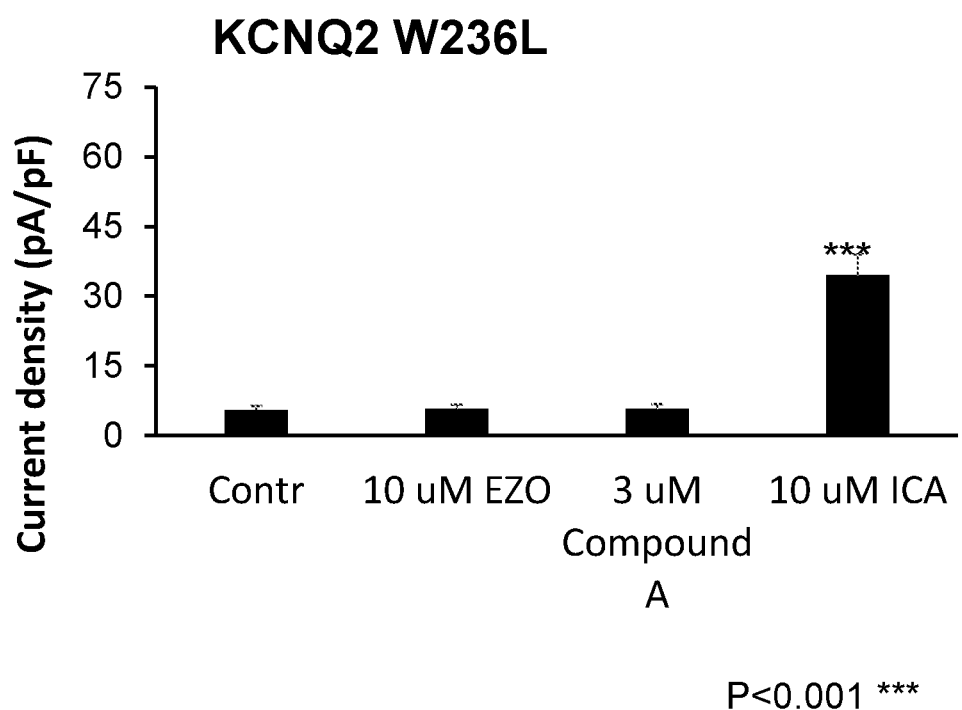
FIG. 14 depicts the current density of KCNQ2 W236L channels after treatment with 10.0 µM of ezogabine, 3.0 µM of Compound A, and 10.0 µM of ICA.
Figure 15:
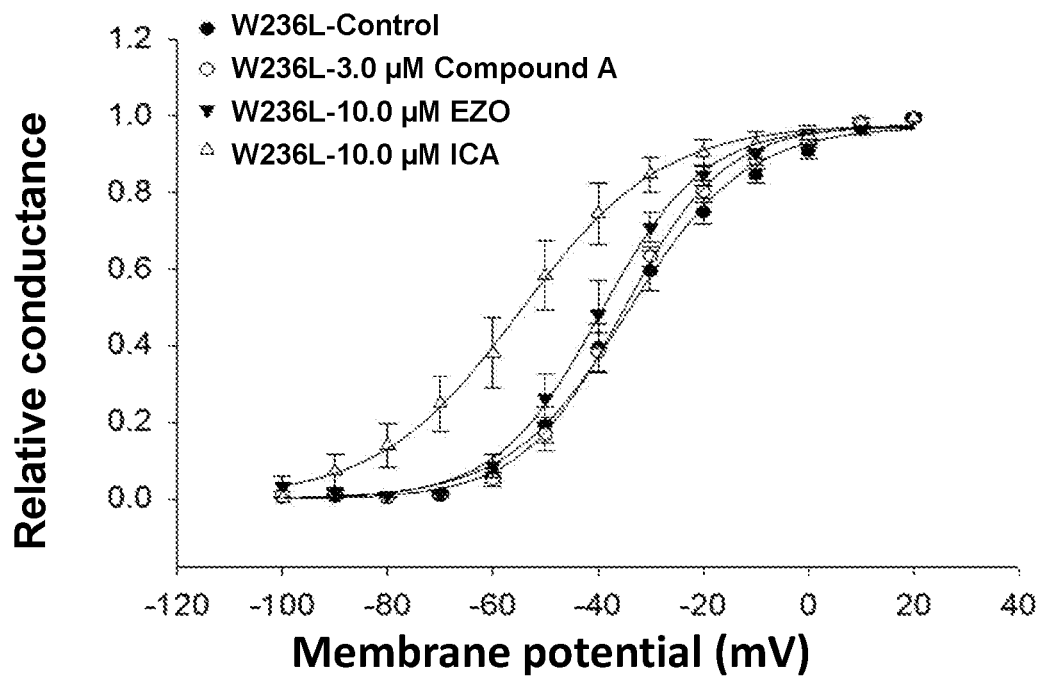
FIG. 15 depicts the effects of Compound A and EZO on the KCNQ2 W236L G/V curve with filled circles representing KCNQ2 W236L, open circles representing KCNQ2 W236L in the presence of 3.0 µM of Compound A, filled triangles representing KCNQ2 W236L in the presence of 10.0 µM of EZO, and open triangles representing KCNQ2 W236L in the presence of 10.0 µM of ICA.
Figure 16:
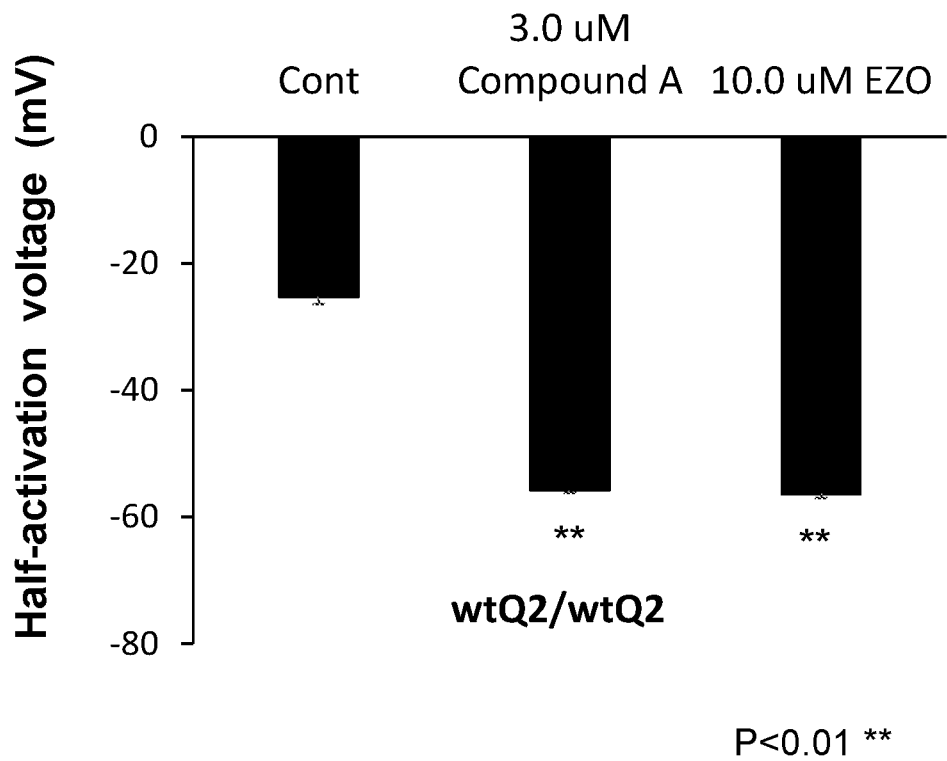
FIG. 16 depicts the half activation voltage (mV) of wild type KCNQ2/wild type KCNQ2 with 3.0 µM of Compound A, and wild type KCNQ2/wild type KCNQ2 with 10.0 µM of EZO.
Figure 17:
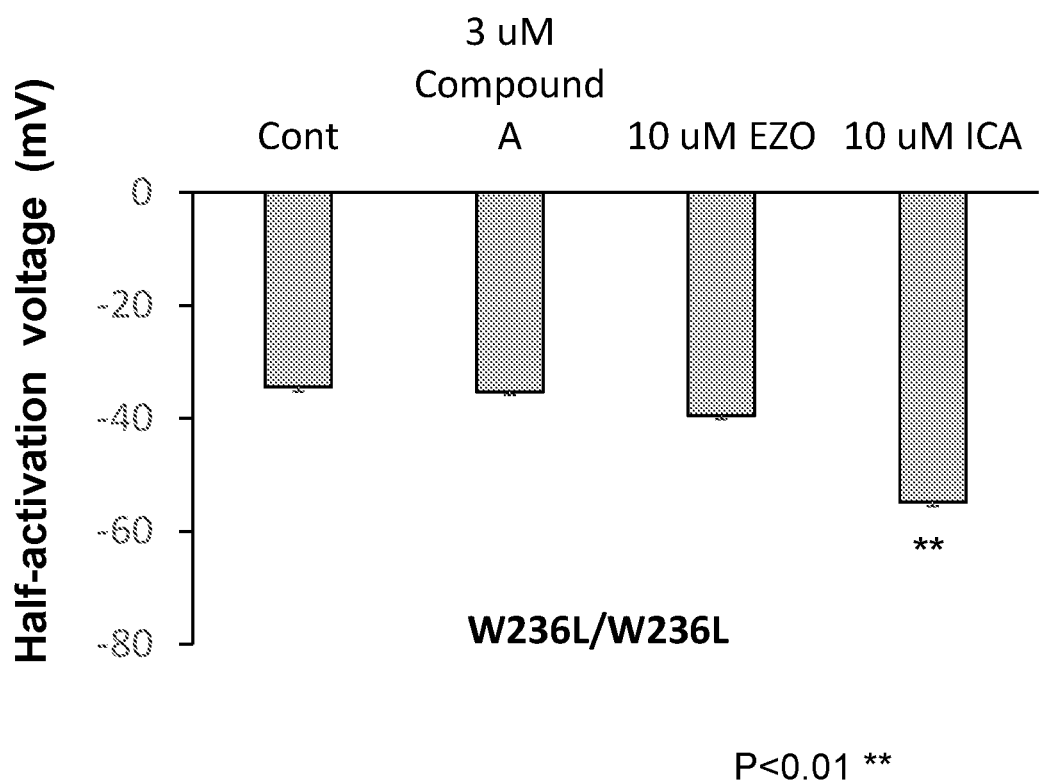
FIG. 17 depicts the half activation voltage (mV) of KCNQ2 W236L, KCNQ2 W236L with 3.0 µM of Compound A, KCNQ2 W236L/KCNQ2 W236L with 10.0 µM of EZO, and KCNQ2 W236L/KCNQ2 W236L with 10.0 µM of ICA.

Example 3: Comparison of Compound A to Ezogabine and ICA-069673 in Activation of KCNQ2 Homomers Compound A activation of KCNQ2 homomers requires W236, like EZO and unlike ICA-069673. (FIG. 10, FIG. 13) representative current traces recorded at −40 mV from cells expressing wildtype KCNQ2 (FIG. 10) and KCNQ2 W236L (FIG. 13) before and after application of drugs. EZO and Compound A increased current density of wildtype KCNQ2 channels (FIG. 11), but did not affect the current density of W236L channels (FIG. 14). Hyperpolarized G/V curves after application of drugs (N=3-12 cells; *<0.05, <0.01 and *<0.001).

Figure 18:
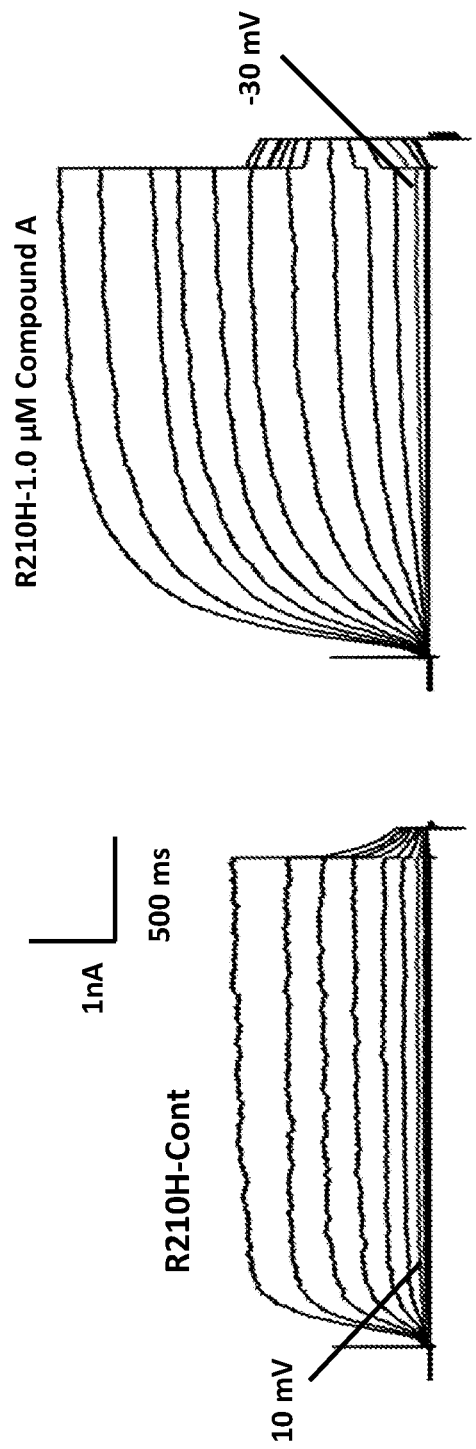
FIG. 18 depicts currents recorded from a cell expressing homomeric R210H channels, before and during application of 1.0 µM Compound A.
Figure 19:
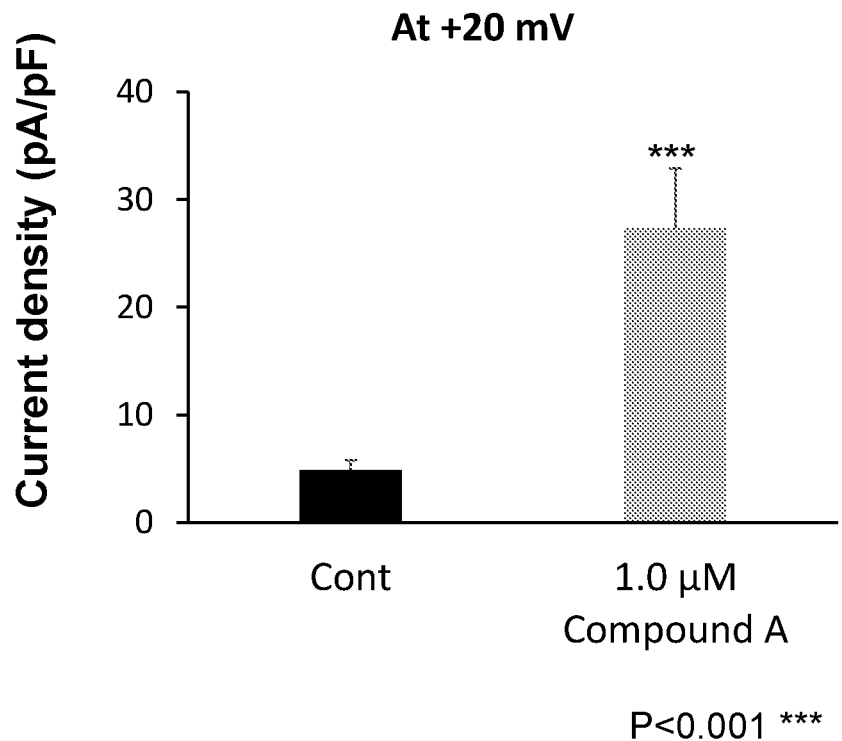
FIG. 19 depicts mean currents at +20 mV before and during treatment with Compound A.
Figure 20:
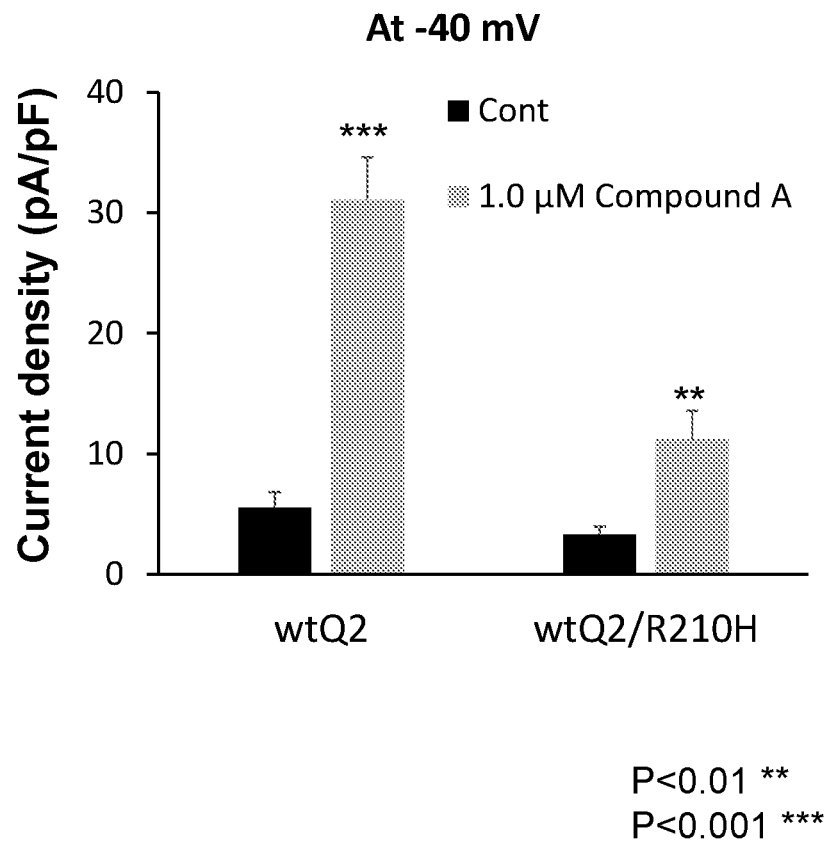
FIG. 20 depicts a comparison of Compound A effects on wild type KCNQ2 and 1:1 co-expressed wild type KCNQ2 and R210H at −40 mV.
Figure 21:
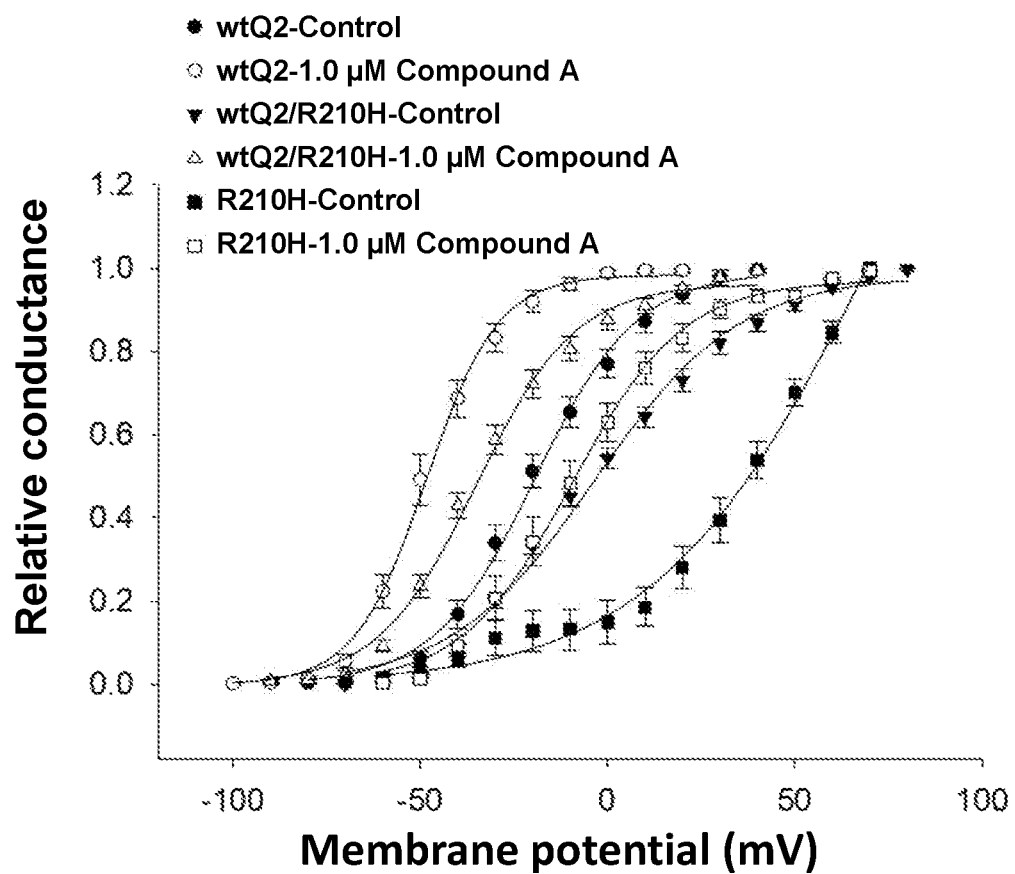
FIG. 21 depicts a summary of $V_{1/2}$ shifts for channels carrying different subunit combinations after application Compound A with filled circles representing wild type KCNQ2, open circles representing wild type KCNQ2 in the presence of 1.0 µM of Compound A, filled triangles representing wild type KCNQ2/R210H, open triangles representing wild type KCNQ2/R210H in the presence of 1.0 µM of Compound A, filled squares representing R210H, and open squares representing R210H in the presence of 1.0 µM of Compound A.
Figure 22:
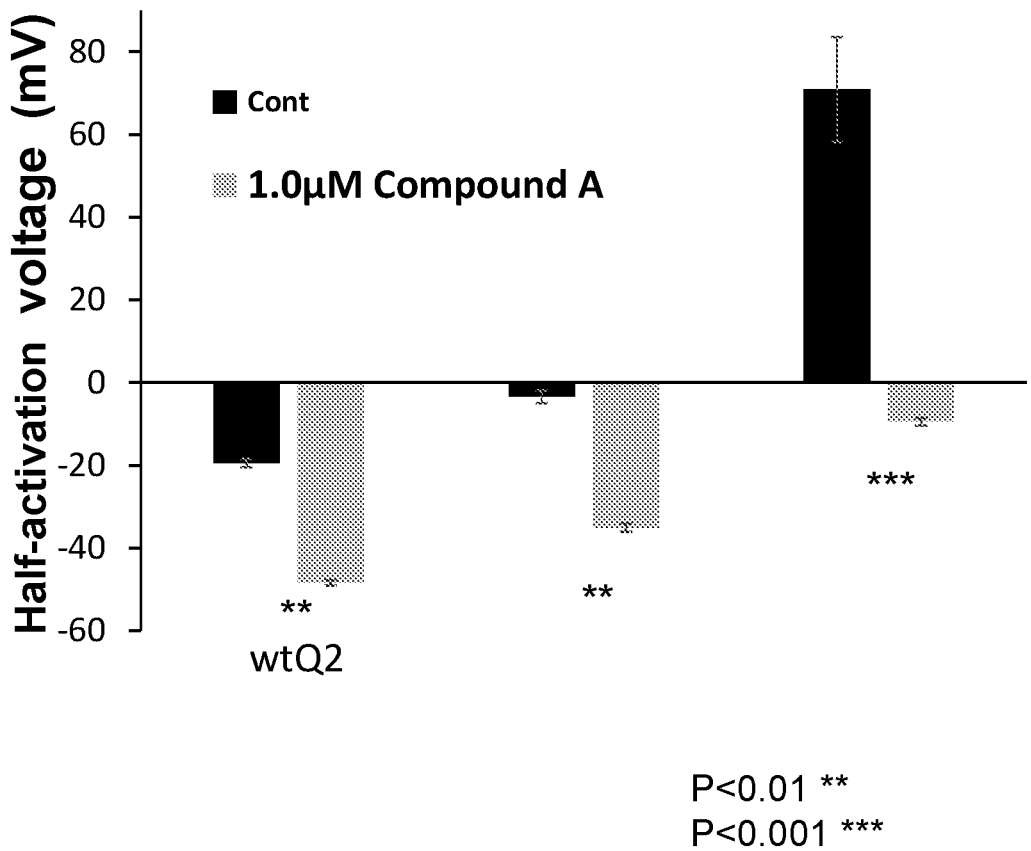
FIG. 22 depicts the half activation voltage (mV) of wild type KCNQ2, wild type KCNQ2/R210H, and R210H each with 1.0 µM of Compound A.

Example 4: Compound A Activation of Channels Incorporating the Recurrent KCNQ2 Voltage Sensor Domain Pathogenic Variant, R210H Compound A activates channels incorporating the recurrent KCNQ2 voltage sensor domain pathogenic variant, R210H. (FIG. 18) Current families recorded from homomeric R210H channels before and after application of 1.0 µM Compound A. R210H activation is very strongly depolarized; this effect is reversed by Compound A. (FIG. 19) Mean currents at +20 mV before and during Compound A application. (FIG. 20) Comparison of Compound A effects on wildtype KCNQ2 and 1:1 coexpressed wildtype and R210H at −40 mV. (FIG. 21, FIG. 22) Summary of V1/2 shifts for channels carrying different subunit combinations after application of 1.0 µM Compound A (N=6-19; *<0.05, <0.01 and *<0.001).

Figure 23:
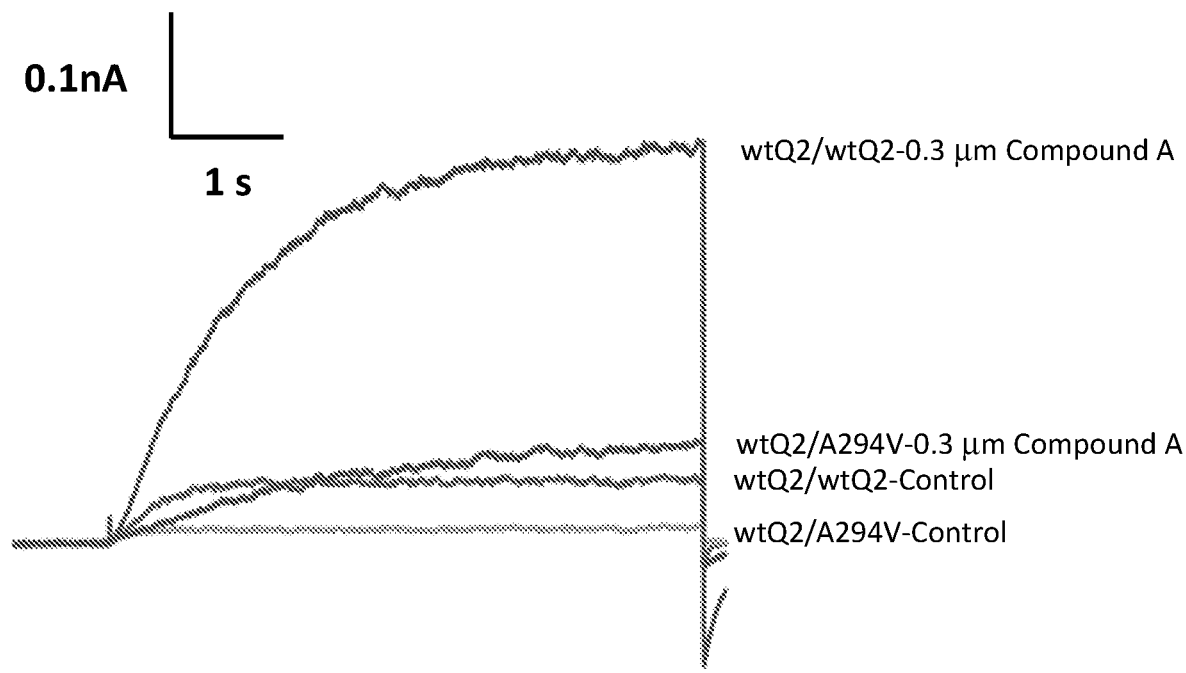
FIG. 23 depicts traces recorded at −40 mV from cells expressing wild type KCNQ2, and from a cell expressing 1:1 KCNQ2 and KCNQ2 A294V, before and during application of 0.3 µM of Compound A.
Figure 24:
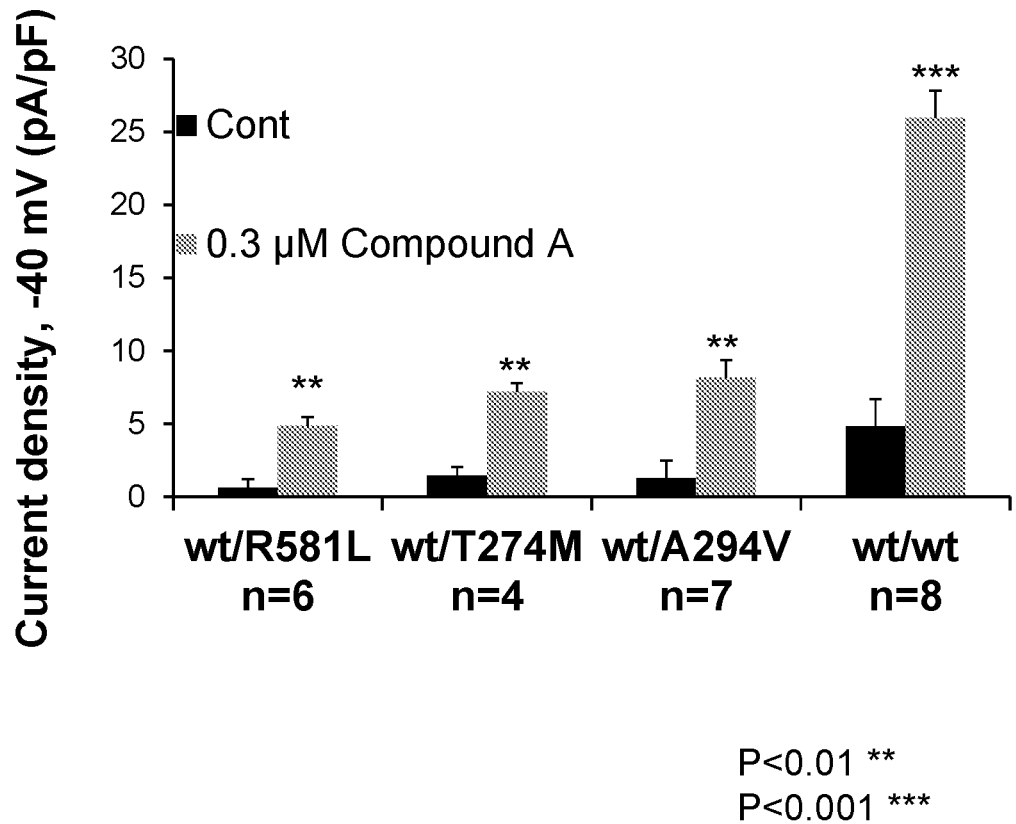
FIG. 24 depicts the effects of 0.3 µM Compound A on current density of wild type KCNQ2 channels and those formed by 1:1 co-expression of wild type KCNQ2 with R581L, T274M, and A294V respectively.

Example 5: Compound A Activation of Homomeric Channels Incorporating Human KCNQ2 Variants Compound A activates homomeric channels incorporating human pathogenic KCNQ2 variants (pore domain and C-terminal). (FIG. 23) Superimposed representative traces recorded at −40 mV from wildtype KCNQ2, and from a cell expressing 1:1 KCNQ2 and KCNQ2 A294V, before and during application of 0.3 µM Compound A. (FIG. 24) Summary of the effects 0.3 µM Compound A on current density of wildtype channels and those formed by 1:1 coexpression of wildtype with the indicated pore domain and C-terminal variants (N=4-8; *<0.05, <0.01 and *<0.001).

Figure 25:
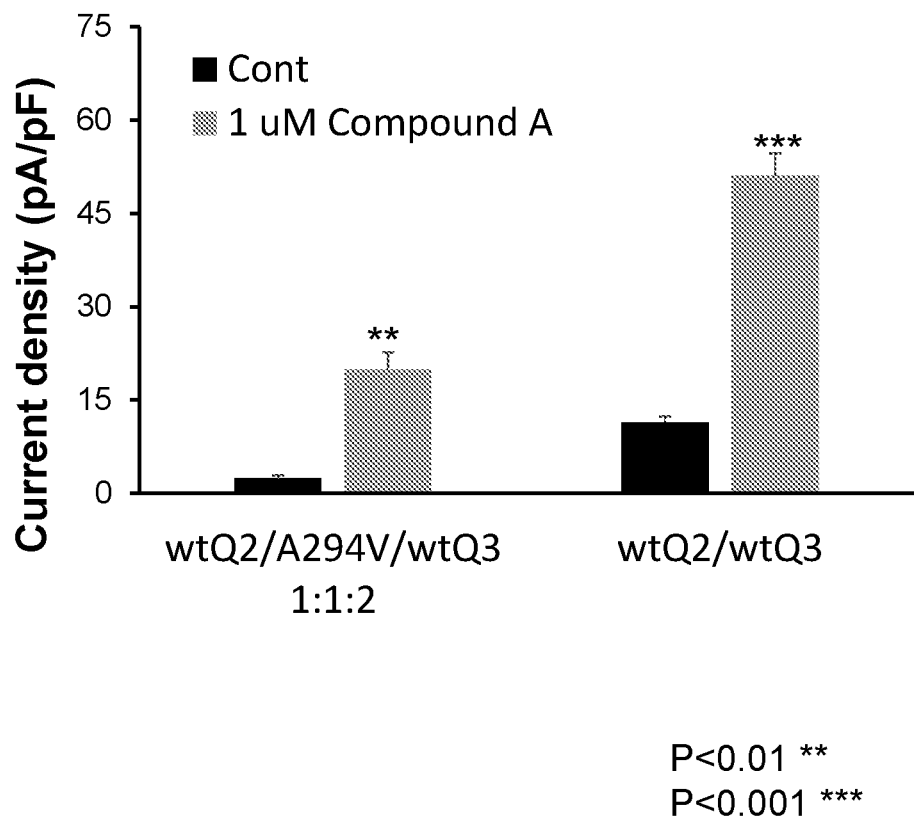
FIG. 25 depicts the current density of wild type KCNQ2/A294V/wild type KCNQ3 (1:1:2 ratio) and wild type KCNQ2/wild type KCNQ3 heteromeric channels after treatment with 1.0 µM of Compound A.
Figure 26:
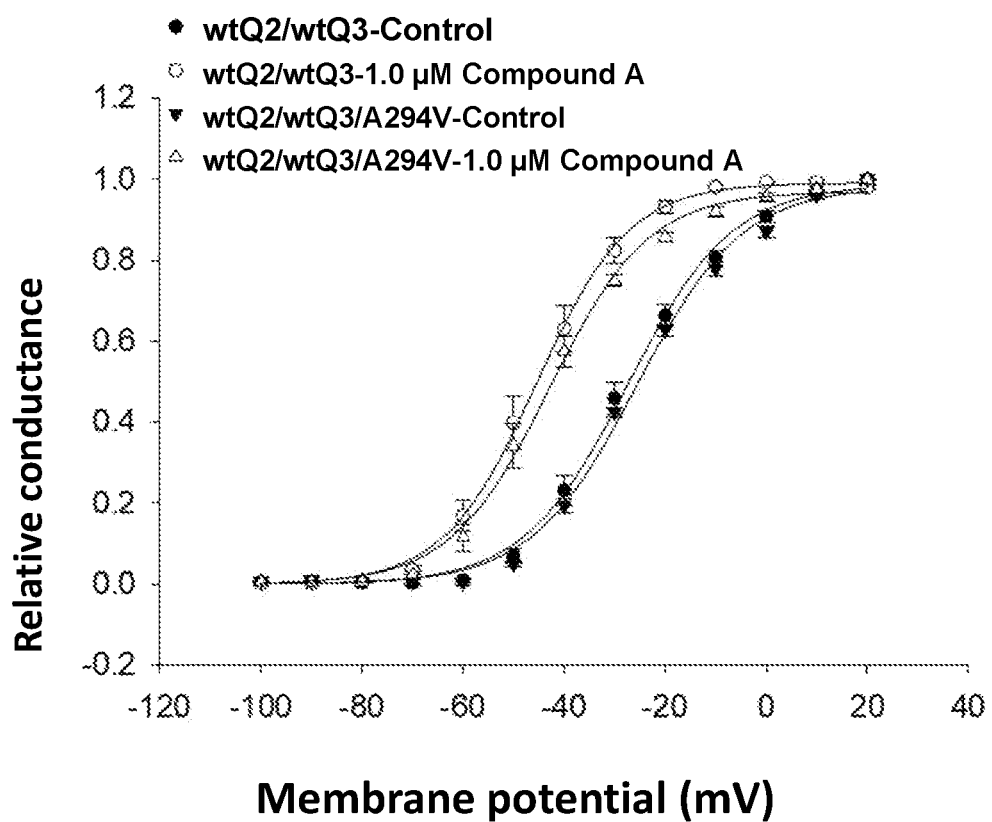
FIG. 26 depicts a summary of $V_{1/2}$ shifts for channels carrying different subunit combinations after application Compound A with filled circles representing wild type KCNQ2/wild type KCNQ3, open circles representing wild type KCNQ2/wild type KCNQ3 in the presence of 1.0 µM of Compound A, filled triangles representing wild type KCNQ2/A294V/wild type KCNQ3 (1:1:2 ratio), and open triangles representing wild type KCNQ2/A294V/wild type KCNQ3 (1:1:2 ratio) in the presence of 1.0 µM of Compound A.
Figure 27:
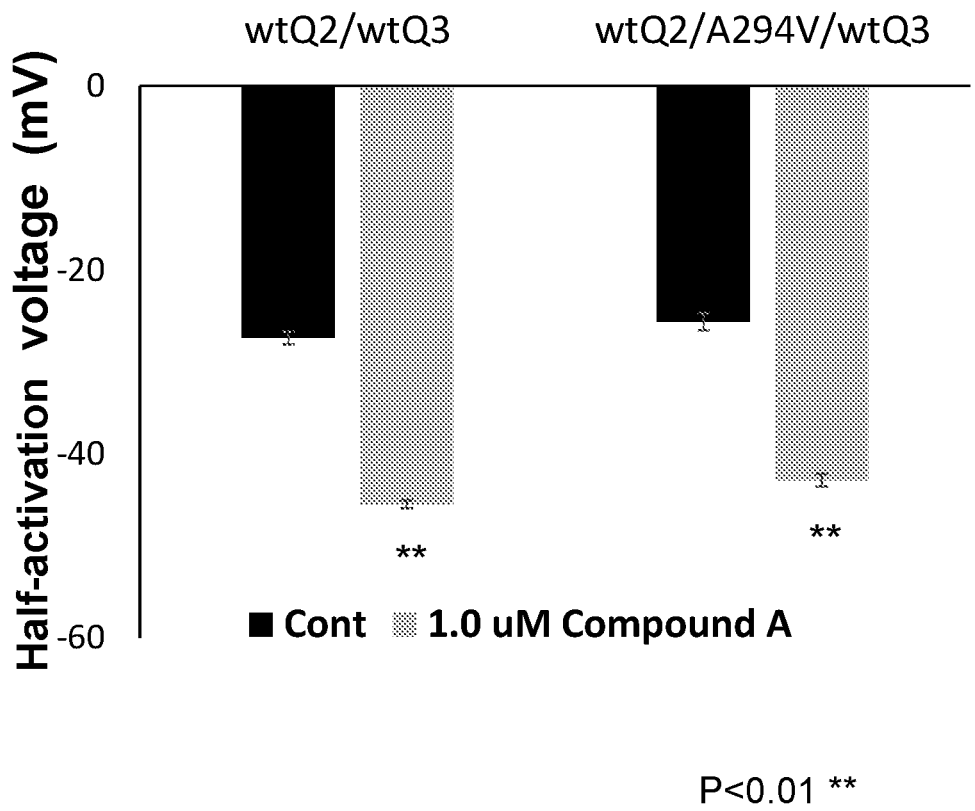
FIG. 27 depicts the half activation voltage (mV) of wild type KCNQ2/wild type KCNQ3 and wild type KCNQ2/A294V/wild type KCNQ3 (1:1:2 ratio) with 1.0 µM of Compound A.
Figure 28:
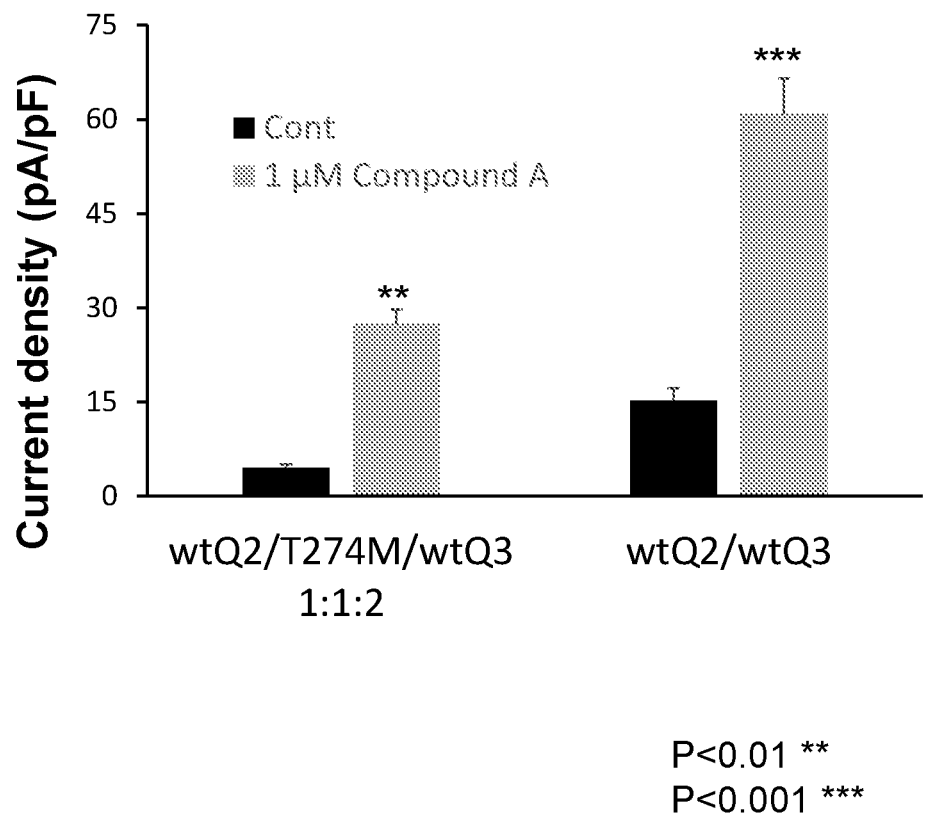
FIG. 28 depicts the current density of wild type KCNQ2/T274M/wild type KCNQ3 (1:1:2 ratio) and wild type KCNQ2/wild type KCNQ3 heteromeric channels after treatment with 1.0 µM of Compound A.
Figure 29:
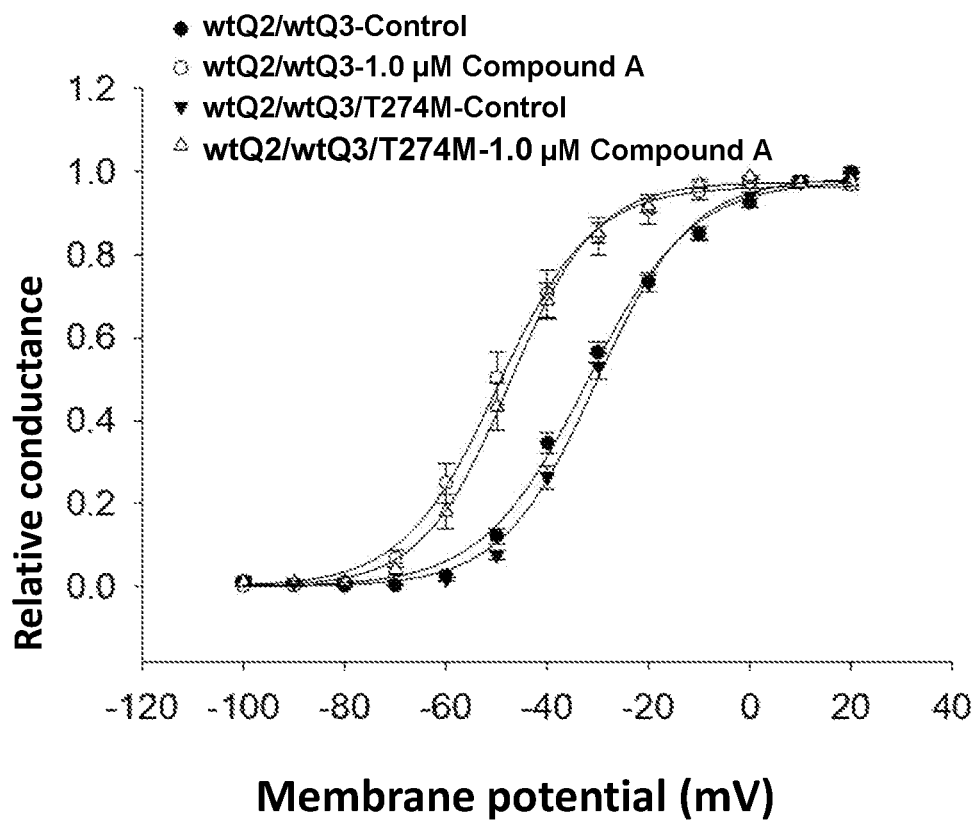
FIG. 29 depicts a summary of $V_{1/2}$ shifts for channels carrying different subunit combinations after application Compound A with filled circles representing wild type KCNQ2/wild type KCNQ3, open circles representing wild type KCNQ2/wild type KCNQ3 in the presence of 1.0 µM of Compound A, filled triangles representing wild type KCNQ2/T274M/wild type KCNQ3 (1:1:2 ratio), and open triangles representing wild type KCNQ2/T274M/wild type KCNQ3 (1:1:2 ratio) in the presence of 1.0 µM of Compound A.
Figure 30:
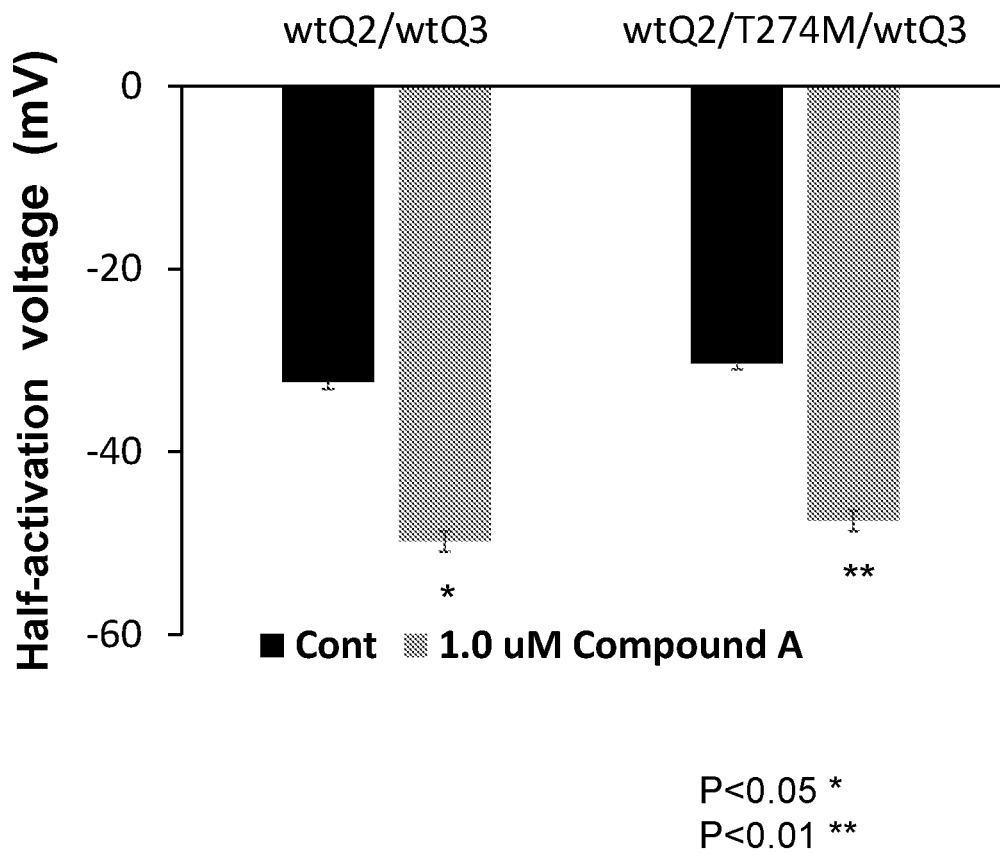
FIG. 30 depicts the half activation voltage (mV) of wild type KCNQ2/wild type KCNQ3 and wild type KCNQ2/T274M/wild type KCNQ3 (1:1:2 ratio) with 1.0 µM of Compound A.

Example 6: Compound A Activation of Heteromeric Channels Incorporating Recurrent Pathogenic KCNQ2 Variants T274M and A294V Compound A activates heteromeric channels incorporating the recurrent pathogenic KCNQ2 variants T274M and A294V (wildtype KCNQ2:variant: wildtype KCNQ3 cDNA ratio=1:1:2 to mimic heterozygosity). Mean current density at −40 mV, conductance/voltage curves, and V1/2 shifts of channels with A294V (FIGS. 25-27) and T274M (FIGS. 28-30), before and during application of 1.0 µM Compound A (N=9-11; *<0.05, <0.01 and *<0.001).

Compound A activates KCNQ2-containing homomers and KCNQ2/3 heteromers by shifting activation and increasing maximal current. Such KCNQ2 modulation requires the pore domain residue W236. Variants from three different KCNQ2-EE mutational hotspots exhibited strong dominant-negative current suppression under conditions mimicking heterozygosity. Compound A (0.3-1 µM) augmented currents in cells expressing each of these variants, increasing currents at −40 mV to wildtype levels. These results suggest potential for benefit in KCNQ2-EE.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of treating a neurodevelopmental disease or disorder comprising administering a therapeutically effective amount of a Compound A, or a pharmaceutically acceptable salt thereof, to a pediatric subject in need thereof,
   wherein Compound A, or a pharmaceutically acceptable salt thereof, is selected from the group consisting of N-(1-cyclobutyl-4-fluoro-6-(1-hydroxycyclobutyl)-1H-benzo[d]imidazol-2-yl)-4,4,4-trifluoro-3,3-dimethylbutanamide; N-(1-(tert-butyl)-6-(difluoromethoxy)-1H-benzo[d]imidazol-2-yl)-3,3-dimethylbutanamide; N-(1-cyclobutyl-4-fluoro-6-(2-hydroxypropan-2-yl)-1H-benzo[d]imidazol-2-yl)-2-(1-methylcyclopropyl) acetamide; N-(7-cyano-1-(1-methylcyclobutyl)-1H-benzo[d]imidazol-2-yl)-3-cyclopropyl-3-methylbutanamide; N-(6-chloro-7-cyano-1-cyclobutyl-1H-benzo[d]imidazol-2-yl)-3,3-dimethylbutanamide; N-(1-(tert-butyl)-6-cyano-4,7-difluoro-1H-benzo[d]imidazol-2-yl)-3,3-dimethylbutanamide; N-(6-cyano-4,7-difluoro-1-(1-methylcyclobutyl)-1H-benzo[d]imidazol-2-yl)-3,3-dimethylbutanamide; N-(1-(tert-butyl)-5,7-difluoro-1H-benzo[d]imidazol-2-yl)-4,4,4-trifluoro-3,3-dimethylbutanamide; and N-(1-(tert-butyl)-5,6-difluoro-1H-benzo[d]imidazol-2-yl)-2-(2,2,3,3-tetrafluorocyclobutyl) acetamide.

2. The method of claim 1, wherein Compound A, or a pharmaceutically acceptable salt thereof, is N-(1-cyclobutyl-4-fluoro-6-(1-hydroxycyclobutyl)-1H-benzo[d]imidazol-2-yl)-4,4,4-trifluoro-3,3-dimethylbutanamide.

3. The method of claim 1, wherein Compound A, or a pharmaceutically acceptable salt thereof, is N-(1-(tert-butyl)-6-(difluoromethoxy)-1H-benzo[d]imidazol-2-yl)-3,3-dimethylbutanamide.

4. The method of claim 1, wherein Compound A, or a pharmaceutically acceptable salt thereof, is N-(1-cyclobutyl-4-fluoro-6-(2-hydroxypropan-2-yl)-1H-benzo[d]imidazol-2-yl)-2-(1-methylcyclopropyl) acetamide.

5. The method of claim 1, wherein Compound A, or a pharmaceutically acceptable salt thereof, is N-(7-cyano-1-(1-methylcyclobutyl)-1H-benzo[d]imidazol-2-yl)-3-cyclopropyl-3-methylbutanamide.

6. The method of claim 1, wherein Compound A, or a pharmaceutically acceptable salt thereof, is N-(6-chloro-7-cyano-1-cyclobutyl-1H-benzo[d]imidazol-2-yl)-3,3-dimethylbutanamide.

7. The method of claim 1, wherein Compound A, or a pharmaceutically acceptable salt thereof, is N-(1-(tert-butyl)-6-cyano-4,7-difluoro-1H-benzo[d]imidazol-2-yl)-3,3-dimethylbutanamide.

8. The method of claim 1, wherein Compound A, or a pharmaceutically acceptable salt thereof, is N-(6-cyano-4,7-difluoro-1-(1-methylcyclobutyl)-1H-benzo[d]imidazol-2-yl)-3,3-dimethylbutanamide.

9. The method of claim 1, wherein Compound A, or a pharmaceutically acceptable salt thereof, is N-(1-(tert-butyl)-5,7-difluoro-1H-benzo[d]imidazol-2-yl)-4,4,4-trifluoro-3,3-dimethylbutanamide.

10. The method of claim 1, wherein Compound A, or a pharmaceutically acceptable salt thereof, is N-(1-(tert-butyl)-5,6-difluoro-1H-benzo[d]imidazol-2-yl)-2-(2,2,3,3-tetrafluorocyclobutyl) acetamide.

11. The method of claim 1, wherein the neurodevelopmental disease or disorder are selected from the group consisting of Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, West syndrome, SCN8A-related epilepsy with encephalopathy (EIEE13), epilepsy of infancy with migrating focal seizures (EIMFS), autosomal dominant nocturnal frontal lobe epilepsy (ADNFLE), Doose syndrome, adrenoleukodystrophy (ALD), ATP6VIA encephalopathy, atypical childhood epilepsy with centrotemporal spikes (ACECTS), autosomal dominant rolandic epilepsy with speech dyspraxia (ADRESD), CDKL5 encephalopathy, childhood epilepsy with centrotemporal spikes (CECTS), Epileptic encephalopathy with continuous spike-and-wave during sleep syndrome (ECSWS), GRIN1 encephalopathy, GRIN2A epilepsy-aphasia syndrome, GRIN2B encephalopathy, intermediate epilepsy-aphasia disorder (IEAD), KCNT1 epilepsy of infancy with migrating focal seizures, neuronal ceroid lipfuscinoses (NCL), non-syndromic developmental and epileptic encephalopathy, PTPN23 enchephalopathy, Rasmussen syndrome, SCN2A-related neonatal epilepsies, STXBP1 encephalopathy, tuberous sclerosis (TS)/tuberous sclerosis complex (TSC), and combinations thereof.

* * * * *